US012697212B2

(12) United States Patent (10) Patent No.: US 12,697,212 B2
Shimel et al. (45) Date of Patent: Aug. 4, 2026

(54) DELIVERY DEVICE

(71) Applicant: INNOVALVE BIO MEDICAL LTD.,
Ramat-Gan (IL)

(72) Inventors: Guy Shimel, Tel Aviv-Jaffa (IL);
Nadav Agian, Kfar Yona (IL); **Eyal
Baror**, Bet Nehemia (IL)

(73) Assignee: INNOVALVE BIO MEDICAL LTD.,
Ramat-Gan (IL)

( * ) Notice: Subject to any disclaimer, the term of this
patent is extended or adjusted under 35
U.S.C. 154(b) by 62 days.

(21) Appl. No.: 17/906,388

(22) PCT Filed: May 4, 2022

(86) PCT No.: PCT/IB2022/054099
§ 371 (c)(1),
(2) Date: Sep. 15, 2022

(87) PCT Pub. No.: WO2022/234468
PCT Pub. Date: Nov. 10, 2022

(65) Prior Publication Data
US 2024/0238089 A1 Jul. 18, 2024

Related U.S. Application Data

(60) Provisional application No. 63/184,403, filed on May
5, 2021, provisional application No. 63/184,427, filed
on May 5, 2021.

(51) Int. Cl.
*A61F 2/24* (2006.01)

(52) U.S. Cl.
CPC .......... *A61F 2/2433* (2013.01); *A61F 2/2427*
(2013.01); *A61F 2/2436* (2013.01); *A61F
2/2466* (2013.01); *A61F 2/24* (2013.01)

(58) Field of Classification Search
CPC .... A61F 2/2427; A61F 2/2436; A61F 2/2466;
A61B 2017/003; A61B 2017/00318
See application file for complete search history.

(56) References Cited

U.S. PATENT DOCUMENTS 6,270,520 B1 8/2001 Inoue
7,018,408 B2 3/2006 Bailey et al.
(Continued)

FOREIGN PATENT DOCUMENTS

CA 2606101 A1 11/2006
CA 2898991 A1 8/2014
(Continued)

OTHER PUBLICATIONS

Advisory Action for U.S. Appl. No. 14/402,387 mailed Mar. 1,
2018.
(Continued)

*Primary Examiner* — Dinah Baria
(74) *Attorney, Agent, or Firm* — Ballard Spahr LLP

(57) ABSTRACT

Apparatus and methods are described for use with a medical
device (21). A delivery device (20) delivers the medical
device (21) to a subject's mitral valve and/or left ventricle.
The delivery device (20) includes a steerable catheter (22)
comprising two or more deflection cables. At least one of the
deflection cables is a steering deflection cable (26) config-
ured to steer the distal portion of the steerable catheter
through a first steerable-catheter deflection plane. At least
one of the deflection cables is a height-adjustment deflection
cable (28) configured to deflect a tip of the steerable catheter,
such that the tip is deflected from within the left atrium
toward a roof of the left atrium, by steering the tip of the
steerable catheter through a second steerable-catheter
deflection plane. Other applications are also described.

16 Claims, 8 Drawing Sheets

(56) References Cited

U.S. PATENT DOCUMENTS

| | | | |
|---|---|---|---|
| 7,621,948 | B2 | 11/2009 | Herrmann et al. |
| 7,748,389 | B2 | 7/2010 | Salahieh et al. |
| 7,753,949 | B2 | 7/2010 | Lamphere et al. |
| 8,070,802 | B2 | 12/2011 | Lamphere et al. |
| 8,870,950 | B2 | 10/2014 | Hacohen |
| 9,364,326 | B2 | 6/2016 | Yaron |
| 9,700,412 | B2 | 7/2017 | Yaron et al. |
| 9,949,830 | B2 | 4/2018 | Solem |
| 10,105,217 | B2 | 10/2018 | Keränen |
| 10,130,471 | B2 | 11/2018 | Keränen et al. |
| 10,238,489 | B2 | 3/2019 | Conklin |
| 10,292,816 | B2 | 5/2019 | Raanani et al. |
| 10,292,850 | B2 | 5/2019 | Vad et al. |
| 10,500,038 | B1 | 12/2019 | Orlov et al. |
| 11,065,114 | B2 | 7/2021 | Raanani et al. |
| 11,583,394 | B2 | 2/2023 | Orlov et al. |
| 11,779,459 | B2 | 10/2023 | Raanani et al. |
| 12,097,114 | B2 | 9/2024 | Raanani et al. |
| 2002/0065554 | A1 | 5/2002 | Streeter |
| 2003/0014104 | A1 | 1/2003 | Cribier |
| 2003/0083742 | A1 | 5/2003 | Spence et al. |
| 2004/0138745 | A1 | 7/2004 | Macoviak et al. |
| 2005/0165479 | A1 | 7/2005 | Drews et al. |
| 2006/0195134 | A1 | 8/2006 | Crittenden |
| 2006/0195184 | A1 | 8/2006 | Lane et al. |
| 2006/0241745 | A1 | 10/2006 | Solem |
| 2007/0016288 | A1 | 1/2007 | Gurskis et al. |
| 2007/0050020 | A1 | 3/2007 | Spence |
| 2007/0260305 | A1 | 11/2007 | Drews et al. |
| 2008/0039935 | A1 | 2/2008 | Buch et al. |
| 2009/0192585 | A1 | 7/2009 | Bloom et al. |
| 2009/0192586 | A1 | 7/2009 | Tabor et al. |
| 2009/0198324 | A1 | 8/2009 | Orlov |
| 2010/0022640 | A1 | 1/2010 | Stoutamire |
| 2010/0030330 | A1 | 2/2010 | Bobo et al. |
| 2010/0042208 | A1 | 2/2010 | Herrmann et al. |
| 2010/0049313 | A1 | 2/2010 | Alon et al. |
| 2010/0249923 | A1 | 9/2010 | Alkhatib et al. |
| 2010/0331971 | A1 | 12/2010 | Keraenen et al. |
| 2011/0029072 | A1 | 2/2011 | Gabbay |
| 2011/0137397 | A1 | 6/2011 | Chau et al. |
| 2011/0137410 | A1 | 6/2011 | Hacohen |
| 2011/0224785 | A1 | 9/2011 | Hacohen |
| 2011/0264208 | A1 | 10/2011 | Duffy et al. |
| 2011/0319989 | A1 | 12/2011 | Lane et al. |
| 2012/0010461 | A1 | 1/2012 | Goldfarb et al. |
| 2012/0022639 | A1 | 1/2012 | Hacohen et al. |
| 2012/0022640 | A1 | 1/2012 | Gross et al. |
| 2012/0101571 | A1 | 4/2012 | Thambar et al. |
| 2013/0035759 | A1 | 2/2013 | Gross et al. |
| 2013/0079873 | A1 | 3/2013 | Migliazza et al. |
| 2013/0166022 | A1 | 6/2013 | Conklin |
| 2013/0190861 | A1 | 7/2013 | Chau et al. |
| 2014/0031928 | A1 | 1/2014 | Murphy et al. |
| 2014/0088695 | A1 | 3/2014 | Figulla et al. |
| 2014/0088696 | A1 | 3/2014 | Figulla et al. |
| 2014/0194975 | A1 | 7/2014 | Quill et al. |
| 2014/0200662 | A1 | 7/2014 | Eftel et al. |
| 2014/0222136 | A1 | 8/2014 | Geist et al. |
| 2014/0222142 | A1 | 8/2014 | Kovalsky et al. |
| 2014/0324164 | A1 | 10/2014 | Gross et al. |
| 2014/0379074 | A1 | 12/2014 | Spence et al. |
| 2015/0045880 | A1 | 2/2015 | Hacohen |
| 2015/0164640 | A1 | 6/2015 | McLean et al. |
| 2015/0173897 | A1 | 6/2015 | Raanani et al. |
| 2015/0265400 | A1 | 9/2015 | Eidenschink et al. |
| 2015/0351903 | A1 | 12/2015 | Morriss et al. |
| 2015/0351908 | A1 | 12/2015 | Kernen et al. |
| 2015/0359628 | A1 | 12/2015 | Keränen |
| 2015/0374493 | A1 | 12/2015 | Yaron et al. |
| 2016/0045306 | A1 | 2/2016 | Agrawal et al. |
| 2016/0095705 | A1 | 4/2016 | Keränen et al. |
| 2017/0128199 | A1 | 5/2017 | Gurovich et al. |
| 2017/0143478 | A1 | 5/2017 | Schwartz et al. |
| 2017/0216023 | A1 | 8/2017 | Lane et al. |

| | | | | |
|---|---|---|---|---|
| 2017/0281338 | A1 | 10/2017 | Quill et al. | |
| 2018/0008404 | A1 | 1/2018 | Tamir | |
| 2018/0014932 | A1 | 1/2018 | Hammer et al. | |
| 2018/0125651 | A1 | 5/2018 | Nasr | |
| 2018/0177594 | A1 | 6/2018 | Patel et al. | |
| 2018/0206992 | A1 | 7/2018 | Brown | |
| 2018/0311037 | A1 | 11/2018 | Morriss et al. | |
| 2018/0318079 | A1* | 11/2018 | Patel | A61M 25/0147 |
| 2019/0083245 | A1 | 3/2019 | Hariton et al. | |
| 2019/0110893 | A1 | 4/2019 | Haarer et al. | |
| 2019/0125534 | A1 | 5/2019 | Arcaro et al. | |
| 2019/0142590 | A1 | 5/2019 | Yeo et al. | |
| 2019/0231520 | A1 | 8/2019 | Desrosiers et al. | |
| 2019/0231522 | A1 | 8/2019 | Raanani et al. | |
| 2020/0100898 | A1 | 4/2020 | Vola et al. | |
| 2020/0121454 | A1 | 4/2020 | Spence | |
| 2020/0138569 | A1 | 5/2020 | Basude et al. | |
| 2020/0179109 | A1 | 6/2020 | Reimer et al. | |
| 2020/0197175 | A1 | 6/2020 | Chang et al. | |
| 2022/0010634 | A1 | 1/2022 | Posa | |
| 2022/0015896 | A1 | 1/2022 | Agian et al. | |
| 2022/0015900 | A1 | 1/2022 | Agian et al. | |
| 2022/0015905 | A1 | 1/2022 | Raanani et al. | |
| 2022/0296370 | A1 | 9/2022 | Agian et al. | |
| 2023/0000622 | A1 | 1/2023 | Raanani et al. | |
| 2023/0172707 | A1 | 6/2023 | Orlov et al. | |
| 2023/0270549 | A1 | 8/2023 | Guidotti et al. | |
| 2023/0372099 | A1 | 11/2023 | Orlov | |
| 2024/0148498 | A1 | 5/2024 | Quadri et al. | |
| 2024/0207045 | A1 | 6/2024 | Orlov et al. | |
| 2025/0268704 | A1 | 8/2025 | Chin | |

FOREIGN PATENT DOCUMENTS

| | | | |
|---|---|---|---|
| CN | 101180010 | A | 5/2008 |
| CN | 102292053 | A | 12/2011 |
| CN | 102438546 | A | 5/2012 |
| CN | 103517688 | A | 1/2014 |
| CN | 104684505 | A | 6/2015 |
| CN | 104994812 | A | 10/2015 |
| DE | 102006052564 | | 12/2007 |
| EP | 1850796 | B1 | 12/2015 |
| EP | 3315094 | A1 | 5/2018 |
| EP | 3399947 | A1 | 11/2018 |
| EP | 2948102 | B1 | 1/2019 |
| EP | 2852354 | B1 | 5/2020 |
| JP | 2008536592 | A | 9/2008 |
| JP | 2011509806 | A | 3/2011 |
| JP | 2012500665 | A | 1/2012 |
| JP | 2012521222 | A | 9/2012 |
| JP | 2014168694 | A | 9/2014 |
| JP | 2015517376 | A | 6/2015 |
| JP | 2016504134 | A | 2/2016 |
| JP | 2018501001 | A | 1/2018 |
| JP | 2019500965 | A | 1/2019 |
| JP | 7051736 | B2 | 4/2022 |
| WO | 0060995 | A2 | 10/2000 |
| WO | 2004032724 | A2 | 4/2004 |
| WO | 2005087140 | A1 | 9/2005 |
| WO | 2006116558 | A2 | 11/2006 |
| WO | 2007135101 | A1 | 11/2007 |
| WO | 2009134701 | A2 | 11/2009 |
| WO | 2010108079 | A1 | 9/2010 |
| WO | 2012004679 | A2 | 1/2012 |
| WO | 2012095116 | A1 | 7/2012 |
| WO | 2013001339 | A2 | 1/2013 |
| WO | 2013028387 | A2 | 2/2013 |
| WO | 2013175468 | A2 | 11/2013 |
| WO | 2014114795 | A1 | 7/2014 |
| WO | 2015198125 | A1 | 12/2015 |
| WO | 2018109329 | A1 | 6/2018 |
| WO | 2018112429 | A1 | 6/2018 |
| WO | 2020092096 | A2 | 5/2020 |
| WO | 2020100050 | A1 | 5/2020 |
| WO | 2021021368 | A1 | 2/2021 |
| WO | 2021028867 | A1 | 2/2021 |
| WO | 2021195090 | A1 | 9/2021 |
| WO | 2022090881 | A1 | 5/2022 |
| WO | 2022090882 | A1 | 5/2022 |

(56)                References Cited

FOREIGN PATENT DOCUMENTS

| WO | 2022234468 A1 | 11/2022 |
| WO | 2022264082 A1 | 12/2022 |
| WO | 2023228028 A1 | 11/2023 |
| WO | 2024057226 A1 | 3/2024 |

OTHER PUBLICATIONS

Communication Pursuant to Article 94(3) EPC Dated Jan. 8, 2018 From the European Patent Office Re. Application No. 13732633.6.

Communication Pursuant to Rule 94(3) for European Patent Application No. 20760551.0 mailed Apr. 7, 2022.

Communication Relating to the Results of the Partial International Search Dated Nov. 18, 2013 From the International Searching Authority Re. Application No. PCT/IL2013/050432.

Corrected Notice of Allowability for U.S. Appl. No. 14/402,387 mailed Mar. 20, 2019.

Examination Report for Australian Application No. 2013264730 mailed Dec. 20, 2017.

Examination Report for Australian Application No. 2013264730 mailed Jan. 13, 2017.

Examination Report for Australian Application No. 2018202951 mailed Dec. 6, 2018.

Examination Report for Australian Application No. 2019250140 mailed Oct. 19, 2020.

Examination Report for European Application No. 13732633.6 mailed Aug. 8, 2019.

Examination Report for Indian Application No. 2424/MUMNP/2014 mailed Aug. 31, 2020.

Final Office Action for U.S. Appl. No. 14/402,387 mailed Oct. 2, 2017.

Final Office Action for U.S. Appl. No. 13/475,994 mailed Jan. 10, 2017.

Final Office Action for U.S. Appl. No. 13/475,994 mailed Jun. 10, 2015.

International Preliminary Report on Patentability from International Application No. PCT/IL2013/050432 mailed Dec. 4, 2014.

International Search Report and Written Opinion for International Application No. PCT/IB2021/059798 mailed Jan. 24, 2022.

International Search Report and Written Opinion for International Application No. PCT/IB2021/059799 mailed Jan. 25, 2022.

International Search Report and Written Opinion from International Application No. PCT/IB2019/059734 mailed Jan. 30, 2020.

International Search Report and Written Opinion from International Application No. PCT/IB2020/057636 mailed Oct. 29, 2020.

International Search Report and Written Opinion from International Application No. PCT/IB2022/054099 mailed Sep. 12, 2022.

International Search Report and Written Opinion from International Application No. PCT/IL2013/050432 mailed Feb. 26, 2014.

Invitation to Pay Additional Fees and, Where Applicable, Protest Fee for International Application No. PCT/IB2022/054099 mailed Jul. 20, 2022.

Issue Notification for U.S. Appl. No. 14/402,387 mailed May 1, 2019.

Issue Notification for U.S. Appl. No. 16/374,240 mailed Jun. 30, 2021.

Non-Final Office Action for U.S. Appl. No. 13/475,994 mailed Apr. 1, 2016.

Non-Final Office Action for U.S. Appl. No. 13/475,994 mailed Oct. 1, 2014.

Non-Final Office Action for U.S. Appl. No. 13/475,994 mailed Sep. 11, 2017.

Non-Final Office Action for U.S. Appl. No. 14/402,387 mailed Dec. 23, 2016.

Non-Final Office Action for U.S. Appl. No. 14/402,387 mailed Sep. 20, 2018.

Non-Final Office Action for U.S. Appl. No. 16/655,656 mailed Jun. 17, 2022.

Notice of Allowance for U.S. Appl. No. 14/402,387 mailed Apr. 30, 2019.

Notice of Allowance for U.S. Appl. No. 14/402,387 mailed Jan. 30, 2019.

Notice of Allowance for U.S. Appl. No. 16/374,240 mailed Mar. 16, 2021.

Notice of Amendment Dated Jun. 23, 2017 From the State Intellectual Property Office of the People's Republic of China Re. Application No. 201710425696.6 and Its Machine Translation Into English.

Notice of Reason for Rejection Dated Feb. 14, 2017 From the Japan Patent Office Re. Application No. 2015-513347 and Translation.

Notification of Office Action and Search Report Dated Sep. 7, 2016 From the State Intellectual Property Office of the People's Republic of China Re. Application No. 201380038199.0.

Notification of Office Action Dated Dec. 3, 2015 From the State Intellectual Property Office of the People's Republic of China Re. Application No. 201380038199.0.

Notification of Office Action Dated Dec. 14, 2016 From the State Intellectual Property Office of the People's Republic of China Re. Application No. 201380038199.0 and Its Translation Into English.

Office Action for Australian Application No. 2018202951 mailed Apr. 1, 2019.

Office Action for Canadian Application No. 2,874,208 mailed Aug. 2, 2019.

Office Action for Canadian Application No. 2,874,208 mailed Feb. 19, 2019.

Office Action for Chinese Application No. 20170425696.6 mailed May 19, 2020.

Office Action for Chinese Application No. 201710425696.6 mailed Nov. 4, 2019.

Office Action for Japanese Application No. 2017-184962 mailed Jul. 31, 2018.

Office Action for Japanese Application No. 2019/032726 mailed Feb. 18, 2020.

Office Action for Japanese Application No. 2019/032726 mailed Jan. 19, 2021.

Office Action for Japanese Application No. 2019/032726 mailed Nov. 19, 2021.

Restriction Requirement for U.S. Appl. No. 13/475,994 mailed Mar. 11, 2014.

Translation Dated Dec. 28, 2015 of Notification of Office Action Dated Dec. 3, 2015 From the State Intellectual Property Office of the People's Republic of China Re. Application No. 201380038199. 0.

Translation of Notification of Office Action and Search Report Dated Sep. 7, 2016 From the State Intellectual Property Office of the People's Republic of China Re. Application No. 201380038199.0.

U.S. Appl. No. 12/582,986, filed Oct. 21, 2009.

U.S. Appl. No. 14/402,387, filed Nov. 20, 2014.

U.S. Appl. No. 16/374,240, filed Apr. 3, 2019.

U.S. Appl. No. 17/263,776, filed Jan. 27, 2021.

U.S. Appl. No. 17/349,152, filed Jun. 16, 2021.

U.S. Appl. No. 17/488,623, filed Sep. 29, 2021.

U.S. Appl. No. 17/488,628, filed Sep. 29, 2021.

U.S. Appl. No. 61/649,319, filed May 20, 2012.

U.S. Appl. No. 62/767,018, filed Nov. 14, 2018.

U.S. Appl. No. 62/886,366, filed Aug. 14, 2019.

U.S. Appl. No. 63/184,403, filed May 5, 2021.

U.S. Appl. No. 63/184,427, filed May 5, 2021.

Applicant-Initiated Interview Summary for U.S. Appl. No. 14/402,387 mailed Dec. 28, 2017.

Applicant-Initiated Interview Summary for U.S. Appl. No. 14/402,387 mailed May 25, 2017.

Final Office Action for U.S. Appl. No. 13/083,643 mailed Mar. 5, 2014.

Final Office Action for U.S. Appl. No. 13/475,994 mailed Jun. 8, 2018.

International Search Report and Written Opinion from International Application No. PCT/IB2023/055160 mailed Jul. 28, 2023.

Issue Notification for U.S. Appl. No. 13/475,994 mailed Nov. 20, 2019.

(56)            References Cited

OTHER PUBLICATIONS

Issue Notification for U.S. Appl. No. 16/655,656 mailed Feb. 1, 2023.
Issue Notification for U.S. Appl. No. 17/349,152 mailed Sep. 20, 2023.
Non-Final Office Action for U.S. Appl. No. 13/475,994 mailed Dec. 28, 2018.
Non-Final Office Action for U.S. Appl. No. 17/263,776 mailed Oct. 25, 2023.
Non-Final Office Action for U.S. Appl. No. 17/488,623 mailed Oct. 26, 2023.
Non-Final Office Action for U.S. Appl. No. 17/488,628 mailed Oct. 26, 2023.
Notice of Allowance for U.S. Appl. No. 13/475,994 mailed Jul. 22, 2019.
Notice of Allowance for U.S. Appl. No. 16/655,656 mailed Oct. 25, 2022.
Office Action for Japanese Application No. 2021-525788 mailed Nov. 1, 2023.
U.S. Appl. No. 13/475,994, filed May 20, 2012.
U.S. Appl. No. 16/655,656, filed Oct. 17, 2019.
U.S. Appl. No. 18/103,671, filed Jan. 31, 2023.
U.S. Appl. No. 61/488,180, filed May 20, 2011.
Examination Report for Indian Application No. 20217021772 mailed Jan. 11, 2023.
Hearing Notice for Indian Application No. 2424/MUMNP/2014 mailed Jan. 3, 2023.
International Search Report and Written Opinion from International Application No. PCT/IB2019/059734 mailed Feb. 6, 2020.
International Search Report and Written Opinion from International Application No. PCT/IB2022/055593 mailed Nov. 14, 2022.
Invitation to Pay Additional Fees for International Application No. PCT/IB2022/055593 mailed Sep. 23, 2022.
U.S. Appl. No. 63/211,602, filed Jun. 17, 2021.
Extended European Search Report for European Application No. 23162937.9 mailed Jun. 21, 2023.
Notice of Allowance for U.S. Appl. No. 17/349,152 mailed May 24, 2023.
Office Action for Canadian Application No. 3,149,527 mailed Mar. 6, 2023.
U.S. Appl. No. 16/106,000, filed Oct. 27, 2020.
U.S. Appl. No. 16/106,034, filed Oct. 27, 2020.
U.S. Appl. No. 18/248,394, filed Apr. 10, 2023.
U.S. Appl. No. 63/106,000, filed Oct. 27, 2020.
U.S. Appl. No. 63/106,034, filed Oct. 27, 2020.
Examination Report for European Application No. 21801644.2 mailed May 2, 2024.
Final Office Action for U.S. Appl. No. 17/488,623 mailed May 30, 2024.
International Search Report and Written Opinion from International Application No. PCT/IB2023/059084 mailed Feb. 12, 2024.
Invitation to Pay Additional Fees for International Application No. PCT/IB2023/059084 mailed Dec. 22, 2023.
Non-Final Office Action for U.S. Appl. No. 17/292,987 mailed May 21, 2024.
Non-Final Office Action for U.S. Appl. No. 17/488,628 mailed May 31, 2024.
Non-Final Office Action for U.S. Appl. No. 18/103,671 mailed Apr. 2, 2024.
Notice of Allowance for U.S. Appl. No. 17/263,776 mailed Apr. 9, 2024.
Notice of Allowance for U.S. Appl. No. 17/932,014 mailed May 22, 2024.
Office Action for Chinese Application No. 201980082413 mailed Jan. 31, 2024.
Office Action for Israel Application No. 283093 mailed Feb. 18, 2024.
Office Action for Japanese Application No. 2021-525788 mailed Mar. 11, 2024.

Office Action for Japanese Application No. 2022-508890 mailed Apr. 9, 2024.
Examination Report for Indian Application No. 202247005897 mailed Dec. 11, 2024.
Final Office Action for U.S. Appl. No. 17/488,628 mailed Jul. 31, 2024.
Final Office Action for U.S. Appl. No. 18/103,671 mailed Jul. 29, 2024.
International Search Report and Written Opinion from International Application No. PCT/IB2024/052304 mailed Jun. 17, 2024.
Issue Notification for U.S. Appl. No. 17/488,628 mailed Oct. 23, 2024.
Issue Notification for U.S. Appl. No. 17/932,014 mailed Sep. 4, 2024.
Issue Notification for U.S. Appl. No. 18/103,671 mailed Jan. 8, 2025.
Non-Final Office Action for U.S. Appl. No. 17/488,623 mailed Jul. 31, 2024.
Notice of Allowance for U.S. Appl. No. 17/292,987 mailed Mar. 5, 2025.
Notice of Allowance for U.S. Appl. No. 17/488,623 mailed Jan. 6, 2025.
Notice of Allowance for U.S. Appl. No. 18/103,671 mailed Sep. 28, 2024.
Office Action for Chinese Application No. 201980082413.X mailed Sep. 26, 2024.
Office Action for Israel Application No. 283093 mailed Jan. 16, 2025.
Office Action for Israel Application No. 290306 mailed Jul. 7, 2024.
U.S. Appl. No. 18/814,988, filed Aug. 26, 2024.
U.S. Appl. No. 18/867,696, filed Nov. 20, 2024.
U.S. Appl. No. 18/994,876, filed Jan. 15, 2025.
U.S. Appl. No. 18/999,207, filed Dec. 23, 2024.
U.S. Appl. No. 63/344,590, filed May 22, 2022.
U.S. Appl. No. 63/405,966, filed Sep. 13, 2022.
Issue Notification for U.S. Appl. No. 17/488,623 mailed Aug. 13, 2025.
U.S. Appl. No. 17/292,987, filed May 11, 2021.
Office Action for Chinese Application No. 202080062891.7 mailed Mar. 5, 2025.
Notice of Allowance for U.S. Appl. No. 17/488,623 mailed Apr. 24, 2025.
Examination Report for European Application No. 22728269.6 mailed Mar. 17, 2025.
Office Action for Israel Application No. 283093 mailed Jul. 20, 2025.
Communication Pursuant to Article 94(3) EPC for European Application No. 21801644.2 mailed Apr. 24, 2025.
Corrected Notice of Allowability for U.S. Appl. No. 17/906,332 mailed Feb. 10, 2026.
Corrected Notice of Allowability for U.S. Appl. No. 17/906,332 mailed Mar. 2, 2026.
Examination Report for European Application No. 19808898.1 mailed Sep. 10, 2025.
Examination Report for European Application No. 21801644.2 mailed Dec. 19, 2025.
Extended European Search Report for European Application No. 22728269.6 mailed Mar. 17, 2025.
International Search Report and Written Opinion from International Application No. PCT/IB2025/056499 mailed Nov. 28, 2025.
Invitation to Pay Additional Fees for International Application No. PCT/IB2025/056499 mailed Oct. 7, 2025.
Non-Final Office Action for U.S. Appl. No. 17/906,332 mailed Sep. 25, 2025.
Non-Final Office Action for U.S. Appl. No. 18/248,394 mailed Nov. 7, 2025.
Non-Final Office Action for U.S. Appl. No. 18/814,988 mailed Dec. 29, 2025.
Notice Before Refusal for Israel Application No. 283093 mailed Jan. 4, 2026.
Notice of Allowance for U.S. Appl. No. 17/906,332 mailed Feb. 2, 2026.

(56)         References Cited

OTHER PUBLICATIONS

Office Action for Chinese Application No. 202180072661.3 mailed
Feb. 9, 2026.
Office Action for Japanese Application No. 2023-566611 mailed
Feb. 20, 2026.
Office Action for Japanese Application No. 2024-157831 mailed
Nov. 20, 2025.
Office Action for Japanese Application No. 2024-192559 mailed
Dec. 8, 2025.
Restriction Requirement for U.S. Appl. No. 18/248,220 mailed Dec.
5, 2025.
U.S. Appl. No. 17/932,014, filed Sep. 14, 2022.

* cited by examiner

DELIVERY DEVICE

CROSS-REFERENCES TO RELATED APPLICATIONS

The present application is a US national phase application of PCT Application No. PCT/IB2022/054099 to Shimel, filed May 4, 2022, entitled "Delivery device," which claims priority from:

U.S. Provisional Patent Application 63/184,403 to Shimel, filed May 5, 2021, entitled "Delivery device," which is incorporated herein by reference; and U.S. Provisional Patent Application 63/184,427 to Shimel, filed May 5, 2021, entitled "Percutaneous introducer sheath," which is incorporated herein by reference.

FIELD OF EMBODIMENTS OF THE INVENTION

The present invention relates to medical apparatus and methods, and specifically to apparatus and methods for percutaneously delivering a medical device to a deployment location within a subject's body, such as an atrioventricular valve.

BACKGROUND

The human heart is a muscular organ that pumps deoxygenated blood through the lungs to oxygenate the blood and pumps oxygenated blood to the rest of the body by contractions of four chambers.

After having circulated in the body, deoxygenated blood from the body enters the right atrium through the vena cava(s). In a healthy subject, the right atrium contracts, pumping the blood through the tricuspid valve into the right ventricle. The right ventricle contracts, pumping the blood through the pulmonary semi-lunar valve into the pulmonary artery which splits to two branches, one for each lung. The blood is oxygenated while passing through the lungs, and reenters the heart via the left atrium. The left atrium contracts, pumping the oxygenated blood through the mitral valve into the left ventricle. The left ventricle contracts, pumping the oxygenated blood through the aortic valve into the aorta to be distributed to the rest of the body. The tricuspid valve closes during right ventricle contraction, so that backflow of blood into the right atrium is prevented. Similarly, the mitral valve closes during left ventricle contraction, so that backflow of blood into the left atrium is prevented. The mitral valve and the tricuspid valve are known as atrioventricular valves, each of these valves controlling the flow of blood between an atrium and a ventricle.

In the mitral valve, the mitral annulus defines a mitral valve orifice. An anterior leaflet and a posterior leaflet extend from the mitral annulus. The leaflets are connected by chords to papillary muscles within the left ventricle. During ventricular diastole, in a healthy subject, the left atrium contracts to pump blood into the left ventricle through the mitral valve orifice. The blood flows through the orifice, pushing the leaflets apart and into the left ventricle with little resistance. In a healthy subject, the leaflets of the aortic valve are kept closed by blood pressure in the aorta.

During ventricular systole, the left ventricle contracts to pump blood into the aorta through the aortic valve, the leaflets of which are pushed open by the blood flow. In a healthy subject, the mitral annulus contracts, pushing the leaflets inwards and reducing the area of the mitral valve orifice by about 20% to 30%. The leaflets coapt to accommodate the excess leaflet surface area, producing a coaptation surface that constitutes a seal. The pressure of blood in the left ventricle pushes against the ventricular surfaces of the leaflets, tightly pressing the leaflets together at the coaptation surface so that a tight, leak-proof seal is formed.

An effective seal of the mitral valve during ventricular systole depends on a sufficient degree of coaptation. Improper coaptation may be caused by any number of physical anomalies that allow leaflet prolapse (for example, elongated or ruptured chords, or weak papillary muscles) or prevent coaptation (for example, short chords, or small leaflets). There are also pathologies that lead to a mitral valve insufficiency, including collagen vascular disease, ischemic mitral regurgitation (resulting, for example, from myocardial infarction, chronic heart failure, or failed/unsuccessful surgical or catheter revascularization), myxomatous degeneration of the leaflets, and rheumatic heart disease. Mitral valve regurgitation leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

There are various medical devices that are configured to be delivered in a minimally-invasive procedure, in which a delivery device is used to deliver the device percutaneously (through a puncture in the skin) to a deployment location at which the device is to be deployed. Many such medical devices are deployed within the subject's vasculature and/or within the subject's heart. For example, such medical devices may include prosthetic valves (e.g., a prosthetic mitral valve, a prosthetic aortic valve, and/or a prosthetic tricuspid valve), valve repair devices (e.g., an annuloplasty ring or an edge-to-edge device, such as a mitral-leaflet clip), stents, hole-closure devices, and/or intravascular simulation devices. Typically, depending on the deployment location, larger medical devices are inserted into the subject's vasculature via the femoral vein or the femoral artery, while smaller devices may also be inserted via the radial vein or the radial artery, or another vein or artery. During delivery of the medical devices to the deployment location, the medical devices are typically maintained in a radially-constrained (i.e., crimped) configuration within the delivery device. The medical devices are radially expanded to their deployment configurations when disposed at the deployment location. In some cases, the medical devices are configured to self-expand, while in other cases the medical devices are radially expanded in an active manner, e.g., via balloon expansion.

There are various medical devices that are configured to be implanted at an atrioventricular valve (such as the mitral valve) and/or within the left ventricle. For example, a prosthetic mitral valve may be deployed to replace the native mitral valve. Or, a mitral valve repair device, such as an annuloplasty ring or a mitral-leaflet clip, may be deployed to repair an unhealthy mitral valve. Some such devices are implanted in an open surgery procedure. Others are implanted in a minimally-invasive procedure, in which a delivery device is used to deliver the device percutaneously to the mitral valve and/or the left ventricle. One approach for percutaneous delivery of a device to the mitral valve and/or the left ventricle is the transseptal approach. Using the transseptal approach, the delivery device is typically inserted into the femoral vein and then advanced through the subject's vena cava and from there through the right atrium and to the interatrial septum. The delivery device then is then made to penetrate the interatrial septum, and is directed toward the mitral valve from within the left atrium.

SUMMARY OF EMBODIMENTS

In accordance with some applications of the present invention, a delivery device is advanced from a subject's vena cava into the subject's right atrium, and from there into the subject's left atrium, via the interatrial septum. The distal end of the delivery device is advanced toward the native mitral valve, and is typically advanced through leaflets of the native mitral valve and into the left ventricle. Typically, the delivery device is used to deliver a percutaneously-implantable medical device, such as a prosthetic mitral valve, a mitral valve repair device (such as an annuloplasty ring or an edge-to-edge device, such as a mitral-leaflet clip), artificial chordae tendineae, and/or a different percutaneously-implantable medical device.

For some applications, the delivery device includes an outer steerable catheter and an inner steerable catheter, and the inner steerable catheter is axially-slidable with respect to the outer steerable catheter. Typically, during advancement of the delivery device from the subject's vena cava into the subject's left atrium, via the interatrial septum, the distal end of the inner steerable catheter is disposed inside the outer steerable catheter. Further typically, once the distal end of the outer steerable catheter is disposed inside the left atrium, the inner steerable catheter is advanced out of the distal end of the outer steerable catheter and then steered toward the subject's mitral valve and/or left ventricle. For some applications, the inner steerable catheter is configured to be steered independently of the outer steerable catheter once the inner steerable catheter has been advanced out of the distal end of the outer steerable catheter.

For some applications, the outer steerable catheter includes first and second steering deflection cables that are configured to be operated by a user to steer the distal end of the outer catheter through a first outer-steerable-catheter deflection plane, toward the subject's interatrial septum. Alternatively, the outer catheter includes only a single steering-deflection cable that is configured to be operated by a user to steer the distal end of the outer steerable catheter through the first outer-steerable-catheter deflection plane toward the subject's interatrial septum. For some applications, in addition to one or more steering deflection cables, the outer catheter includes a height-adjustment deflection cable. Typically, the height-adjustment deflection cable is configured to be operated by a user to deflect the distal end of the outer steerable catheter from within the left atrium toward the roof of the left atrium, by steering the tip of the outer steerable catheter through a second outer-steerable-catheter deflection plane. Further typically, the second outer-steerable-catheter deflection plane is perpendicular to the first outer-steerable-catheter deflection plane. Accordingly, height-adjustment deflection cable is typically disposed at a 90 degree angle with respect to the steering-deflection cable(s).

Typically, the delivery device includes a capsule at its distal end. Further typically, the percutaneously-implantable medical device is held in a crimped (i.e., radially-constrained) configuration inside the capsule, during delivery of the medical device to the subject's mitral valve and/or left ventricle. In order to deploy the device at the subject's mitral valve and/or left ventricle, the medical device is released from the capsule, as described in further detail hereinbelow. For some applications, the medical device is a self-expandable medical device that is configured to self-expand radially upon being released from the capsule. For example, the medical device may include a shape-memory alloy (such as nitinol) that is shape set to a desired radially-expanded configuration. Alternatively or additionally, the device may actively be radially expanded after being released from the capsule (e.g., via balloon expansion).

For some applications, the capsule includes a distal capsule portion configured to maintain a distal portion of the medical device in the radially-constrained configuration during delivery of the medical device to the deployment location, and a proximal capsule portion configured to maintain a proximal portion of the medical device in a radially-constrained configuration during delivery of the medical device to the deployment location. Typically, the proximal and distal portions are reversibly couplable to each other. Further typically, once the medical device has been released from within the capsule, the proximal and distal portions of the capsule are re-coupled to each other before being retracted from within the subject's body.

For some applications, the capsule includes a guide portion defined by at least one of the distal and proximal capsule portions. The guide portion is configured to guide the distal and proximal capsule portions back into their coupled configuration, subsequent to the medical device having been deployed. For example, for some applications, the proximal capsule portion defines a lip at its distal end, and the distal capsule portion defines a corresponding lip at is proximal end, with the lips being shaped such as to slide into place with respect to each other. Alternatively, only one of the capsule portions defines a lip, and the lip is configured to receive the other capsule portion. Typically, when the proximal and distal portions are correctly coupled to each other they are shaped such as to define a substantially smooth outer surface. In this manner, during advancement of the capsule to the medical device deployment location, the capsule is atraumatic and does not cause damage to tissue of the subject. Similarly, during retraction of the capsule from the medical device deployment location, the capsule is atraumatic and does not cause damage to tissue of the subject or to the deployed medical device. For some applications, the above-mentioned lip is formed as a complete ring. For some applications, a lip that is generally as described above is split into multiple, separate, arc-shaped, segments. For example, the lip may be formed from 4 arc-shaped segments, spaced 90 degrees apart from each other and each covering an arc of 30 degrees. In this way the medical device may be released before the entire capsule is removed, hence saving on the height that is required to release the medical device.

For some applications, a handle of the delivery device includes a rotational control component that is configured to transmit rotational motion to the capsule. A nut is disposed within the capsule, and is configured to convert the rotational motion to axial motion of a portion of the capsule, to thereby release at least a portion of the medical device from within the capsule.

In accordance with some applications, a delivery device is used to deliver a medical device in a minimally-invasive procedure, in which the medical device is inserted percutaneously (through a puncture in the skin) to a deployment location at which the device is to be deployed. Typically, the delivery device is inserted through the puncture in the patient's skin via a percutaneous introducer sheath. For some applications, the delivery device includes a capsule at its distal end (e.g., a capsule as described herein), and the capsule is configured to house the medical device in its radially-constrained (i.e., crimped) configuration during delivery of the medical device to deployment location. For some such applications, the capsule is greater in diameter than a portion of the delivery device that is proximal to the capsule (e.g., a steerable catheter, as described herein). In some cases, the difference in the diameter between the capsule and the portion of the delivery device that is proximal to the capsule can give rise to bleeding after the capsule has been advanced through the vascular puncture. This is because the vascular puncture is widened by the insertion of the capsule, such that the vascular walls surrounding the puncture do not seal against the portion of the delivery device that is proximal to the capsule and narrower than the capsule. Such problems may also arise with other forms of delivery devices having a widened distal portion and a proximal portion that is narrower than the widened distal portion. The scope of the present application is applicable to all such delivery devices, mutatis mutandis.

In accordance with some applications of the present invention, the percutaneous introducer sheath is made of a stretchable material (e.g., an elastomer, such as silicone, or polyurethane). As described in further detail hereinbelow, the percutaneous introducer sheath defines a lumen, which in the non-stretched state of the percutaneous introducer sheath is sized such as to accommodate the portion of the delivery device that is proximal to the capsule. Further typically, in the non-stretched state of the percutaneous introducer sheath, the outer diameter of the sheath is approximately equal to or greater than the outer diameter of the capsule. For some applications, any difference between the outer diameter of the percutaneous introducer sheath and the outer diameter of the capsule is less than 20 percent (e.g., less than 5 percent, or less than 2 percent) of the outer diameter of the capsule. Before inserting the percutaneous introducer sheath into the subject's body, the capsule is typically advanced through the lumen defined by the percutaneous introducer sheath by stretching the percutaneous introducer sheath, such that the entire capsule is disposed distally of the distal end of the percutaneous introducer sheath. The capsule is then advanced through the subject's skin and into the subject's vasculature, followed by the percutaneous introducer sheath. Typically, even after the vascular puncture has been widened by the capsule, the vascular walls surrounding the puncture seal against the outside of the percutaneous introducer sheath, since the outer diameter of the sheath is approximately equal to or greater than the outer diameter of the capsule. For some applications, during the advancement of the delivery device through the subject's vasculature, the percutaneous introducer sheath is disposed such that it remains within the punctures in the subject's skin and vasculature, and the portion of the delivery device that is proximal to the capsule is advanced through the lumen defined by the percutaneous introducer sheath.

It is noted that, by virtue of the introducer sheath being stretchable, the introducer sheath can be loaded onto the delivery device in the setting in which the procedure takes place (e.g., in the catheterization laboratory). As described above, within this setting and before inserting the percutaneous introducer sheath into the subject's body, the capsule is typically advanced through the lumen of the percutaneous introducer sheath by stretching the percutaneous introducer sheath, such that the entire capsule is disposed distally of the distal end of the percutaneous introducer sheath. By contrast, if the introducer sheath were not sufficiently stretchable, the introducer sheath would have to be placed around the portion of the delivery device that is proximal to the capsule in a clean room, prior to the procedure, as part of the assembly process of the delivery device (or a capsule having a smaller diameter would be required).

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

There is therefore provided, in accordance with some applications of the present invention, apparatus for use with a medical device including:

a delivery device configured to deliver the medical device to a mitral valve and/or a left ventricle of a subject, the delivery device including:

a steerable catheter including two or more deflection cables, at least one of the deflection cables being a steering deflection cable configured to steer a distal portion of the steerable catheter from a vena cava of the subject through a right atrium and an interatrial septum of the subject and into a left atrium of the subject, by steering the distal portion of the steerable catheter through a first steerable-catheter deflection plane, and at least one of the deflection cables being a height-adjustment deflection cable configured to deflect a tip of the steerable catheter relative to a portion of the steerable catheter that is proximal to the tip, such that the tip is deflected from within the left atrium toward a roof of the left atrium, by steering the tip of the steerable catheter through a second steerable-catheter deflection plane.

In some applications, the height-adjustment deflection cable is disposed at a 90 degree angle with respect to the steering deflection cable.

In some applications, the steering deflection cable is configured to steer the distal portion of the steerable catheter through the first steerable-catheter deflection plane through an angle of between 0 degrees and more than 60 degrees, to steer the distal portion of the steerable catheter from the vena cava through the right atrium and the interatrial septum of the subject and into the left atrium of the subject.

In some applications, the height-adjustment deflection cable is configured to steer the tip of the steerable catheter through the second steerable-catheter deflection plane through an angle of between 0 degrees and more than 30 degrees, to deflect the tip of the steerable catheter relative to the portion of the steerable catheter that is proximal to the tip.

In some applications, the steerable catheter includes an outer steerable catheter, and the delivery device further includes an inner steerable catheter that is disposed within the outer steerable catheter and a distal portion of which is configured to be advanceable out of a distal end of the outer steerable catheter and to be steered independently of the outer steerable catheter.

In some applications, the inner steerable catheter includes a first set of one or more steering deflection cables that are configured to steer a distal end of the inner steerable catheter through a first inner-steerable-catheter deflection plane toward the subject's mitral valve, and a second set of one or more steering deflection cables that are configured to steer the distal end of the inner steerable catheter through a second inner-steerable-catheter deflection plane, such as to align the distal end of the inner steerable catheter with the subject's mitral valve.

In some applications, the first set of one or more steering deflection cables are configured to steer the distal end of the inner steerable catheter through the first inner-steerable-catheter deflection plane through an angle of between 0 degrees and more than 80 degrees, to steer the distal end of the inner steerable catheter toward the subject's mitral valve.

In some applications, the second set of one or more steering deflection cables are configured to steer the distal end of the inner steerable catheter through the second inner-steerable-catheter deflection plane through an angle of at least between −45 degrees and +45 degrees, to align the distal end of the inner steerable catheter with the subject's mitral valve.

In some applications, the first set of one or more steering deflection cables is disposed at a 90 degree angle with respect to the second set of one or more steering deflection cables.

In some applications, the delivery device further includes a capsule configured to house the medical device during delivery of the medical device to the mitral valve and/or the left ventricle and configured to maintain the medical device in a radially-constrained configuration during delivery of the medical device to the mitral valve and/or the left ventricle.

In some applications, the capsule includes:

a distal capsule portion configured to maintain a distal portion of the medical device in a radially-constrained configuration during delivery of the medical device to the mitral valve and/or the left ventricle; and a proximal capsule portion configured to maintain a proximal portion of the medical device in a radially-constrained configuration during delivery of the medical device to the mitral valve and/or the left ventricle.

In some applications, a proximal end of the proximal capsule portion defines a recess, such that the proximal end of the proximal capsule portion is configured to be retracted such as to overlap with a distal end of the inner steerable catheter.

There is further provided, in accordance with some applications of the present invention, a method for delivering a medical device to a mitral valve and/or a left ventricle of a subject, the method including:

inserting a delivery device into a vena cava of the subject, the delivery device including at least one steerable catheter;

steering a distal portion of steerable catheter from the subject's vena cava through an interatrial septum of the subject and into a left atrium of the subject, by steering the distal portion of the steerable catheter through a first steerable-catheter deflection plane;

deflecting a tip of the steerable catheter from within the left atrium toward a roof of the left atrium, by steering the tip of the steerable catheter through a second outer-steerable-catheter deflection plane;

advancing the medical device beyond the tip of the outer steerable catheter; and steering the medical device from the tip of the steerable catheter toward the subject's mitral valve.

There is further provided, in accordance with some applications of the present invention, apparatus for use with a medical device including:

a delivery device configured to deliver the medical device to a deployment location within a body of a subject, the delivery device including:

a capsule configured to house the medical device during delivery of the medical device to the deployment location and configured to maintain the medical device in a radially-constrained configuration during delivery of the medical device to the deployment location;

a handle including a rotational control component that is configured to transmit rotational motion to the capsule;

a motion-conversion mechanism disposed within the capsule, the motion-conversion mechanism being configured to convert the rotational motion to axial motion of a portion of the capsule, to thereby release at least a portion of the medical device.

In some applications, the motion-conversion mechanism includes a screw-and-nut mechanism.

In some applications, the capsule includes:

a distal capsule portion configured to maintain a distal portion of the medical device in a radially-constrained configuration during delivery of the medical device to the deployment location; and a proximal capsule portion configured to maintain a proximal portion of the medical device in a radially-constrained configuration during delivery of the medical device to the deployment location.

In some applications, the delivery device further includes a delivery catheter, and a proximal end of the proximal capsule portion defines a recess, such that the proximal end of the proximal capsule portion is configured to be retracted such as to overlap with a distal end of the delivery catheter.

In some applications:

the distal capsule portion is coupled to a first shaft;

the delivery device further includes a distal device interface configured to secure a distal portion of the medical device, the distal device interface being coupled to a second shaft; and the motion-conversion mechanism is configured to cause rotational motion of the first shaft relative to the second shaft to result in axial motion of the first shaft relative to the second shaft, to thereby cause the distal capsule portion to move axially relative to the distal portion of the medical device.

In some applications, the delivery device further includes a bearing mechanism that is configured to separate rotational motion of the distal capsule portion from rotational motion of the first shaft.

In some applications, the motion-conversion mechanism includes a screw-and-nut mechanism.

In some applications, a surface of the first shaft is threaded and a surface of the second shaft is threaded, such that rotational motion of the first shaft relative to the second shaft to result in axial motion of the first shaft relative to the second shaft.

In some applications, a surface of the first shaft is threaded and a surface of the distal device interface is threaded, such that rotational motion of the first shaft relative to the second shaft to result in axial motion of the first shaft relative to the second shaft.

There is further provided, in accordance with some applications of the present invention, apparatus for use with a medical device including:

a delivery device configured to deliver the medical device to a deployment location within a body of a subject, the delivery device including:

a capsule configured to house the medical device during delivery of the medical device to the deployment location, the capsule including:

a distal capsule portion configured to maintain a distal portion of the medical device in a radially-constrained configuration during delivery of the medical device to the deployment location, the distal capsule portion being coupled to a first shaft;

a proximal capsule portion configured to maintain a proximal portion of the medical device in a radially-constrained configuration during delivery of the medical device to the deployment location;

a distal device interface configured to secure a distal portion of the medical device, the distal device interface being coupled to a second shaft;

a handle including a rotational control component that is configured to transmit rotational motion to the first shaft;

a motion-conversion mechanism disposed within the distal capsule portion, the motion-conversion mechanism being configured to cause rotational motion of the first shaft relative to the second shaft to result in axial motion of the first shaft relative to the second shaft, to thereby cause the distal capsule portion to move axially relative to the distal portion of the medical device.

There is further provided, in accordance with some applications of the present invention, apparatus for use with a medical device including:

a delivery device configured to deliver the medical device to a deployment location within a body of a subject, the delivery device including:

a distal capsule portion configured to maintain a distal portion of the medical device in a radially-constrained configuration during delivery of the medical device to the deployment location;

a proximal capsule portion configured to maintain a proximal portion of the medical device in a radially-constrained configuration during delivery of the medical device to the deployment location, the distal and proximal capsule portions being configured to be reversibly couplable to each other, such that (a) the distal and proximal capsule portions define a coupled configuration in which the distal and proximal capsule portions define a substantially smooth outer surface, the distal and proximal capsule portions being configured to be disposed in the coupled configuration during delivery of the medical device to the deployment location and (b) the distal and proximal capsule portions are separable from each other, such as to deploy the medical device, by releasing the distal and proximal portions of the medical device from their radially-constrained configurations; and a guide portion defined by at least one of the distal and proximal capsule portions, the guide portion being configured to guide the distal and proximal capsule portions back into their coupled configuration, subsequent to the medical device having been deployed.

In some applications, the guide portion includes lips disposed at ends of the distal and proximal capsule portions that are configured to overlap with each other in the coupled configuration of the distal and proximal capsule portions.

In some applications, the delivery device further includes a delivery catheter, and a proximal end of the proximal capsule portion defines a recess, such that the proximal end of the proximal capsule portion is configured to be retracted such as to overlap with a distal end of the delivery catheter.

There is further provided, in accordance with some applications of the present invention, apparatus for use with a delivery device that includes a widened distal portion and a proximal portion that is narrower than the widened distal portion, the apparatus including:

an introducer sheath that defines a lumen therethrough and that is configured to facilitate introduction of the delivery device through a vascular puncture, the introducer sheath including a stretchable material, and the introducer sheath being sized such that:

by the introducer sheath being stretched, the widened distal portion of the delivery device is insertable through the lumen defined by the introducer sheath, in its non-stretched state, the lumen is able to accommodate the proximal portion of the delivery device, and in its non-stretched state, an outer diameter of the introducer sheath at its distal end is approximately equal to or greater than an outer diameter of the widened distal portion of the delivery device.

In some applications, the apparatus is for use with a delivery device that includes a capsule that is configured to house a medical device during delivery of the medical device to the deployment location and a delivery catheter disposed proximally with respect to the capsule and that is narrower than the capsule.

In some applications, the introducer sheath is configured such that, before inserting the introducer sheath into a subject's body, the widened distal portion of the delivery device is advanced through the lumen of the introducer sheath by stretching the introducer sheath, such that the entire widened distal portion is disposed distally of a distal end of the introducer sheath.

In some applications, the introducer sheath includes a femoral introducer sheath configured to be inserted into a femoral blood vessel of the subject, and a total length of the introducer sheath is between 60 and 120 mm. In some applications, a diameter of the lumen defined by the introducer sheath is between 7 and 10 mm. In some applications, an outer diameter of the introducer sheath at its distal end is between 8 and 12 mm. In some applications, a diameter of the lumen defined by the introducer sheath is between 7 and 10 mm.

In some applications, in the non-stretched state of the introducer sheath, a difference between the outer diameter of the introducer sheath at its distal end and the outer diameter of the widened distal portion of the delivery device is less than 20 percent of the outer diameter of the widened distal portion of the delivery device. In some applications, in the non-stretched state of the introducer sheath, a difference between the outer diameter of the outer diameter of the introducer sheath at its distal end and the outer diameter of the widened distal portion of the delivery device is less than 5 percent of the outer diameter of the widened distal portion of the delivery device. In some applications, in the non-stretched state of the introducer sheath, any difference between the outer diameter of the outer diameter of the introducer sheath at its distal end and the outer diameter of the widened distal portion of the delivery device is less than 2 percent of the outer diameter of the widened distal portion of the delivery device.

There is further provided, in accordance with some applications of the present invention, apparatus for use with a medical device including:

a delivery device configured to deliver the medical device to a deployment location within a body of a subject, the delivery device including:
delivery catheter; and
a capsule disposed at a distal end of the delivery catheter, the capsule being configured to house the medical device during delivery of the medical device to the deployment location and configured to maintain the medical device in a radially-constrained configuration during delivery of the medical device to the deployment location,
a proximal end of the capsule defining a recess, such that the proximal end of the capsule is configured to be retracted such as to overlap with the distal end of the delivery catheter.
In some applications:
the capsule includes:
a distal capsule portion configured to maintain a distal portion of the medical device in a radially-constrained configuration during delivery of the medical device to the deployment location;
a proximal capsule portion configured to maintain a proximal portion of the medical device in a radially-constrained configuration during delivery of the medical device to the deployment location, and
a proximal end of the proximal capsule portion defines the recess.
The present invention will be more fully understood from the following detailed description of applications thereof, taken together with the drawings, in which:

DETAILED DESCRIPTION OF EMBODIMENTS

Figures 1A, 1B:
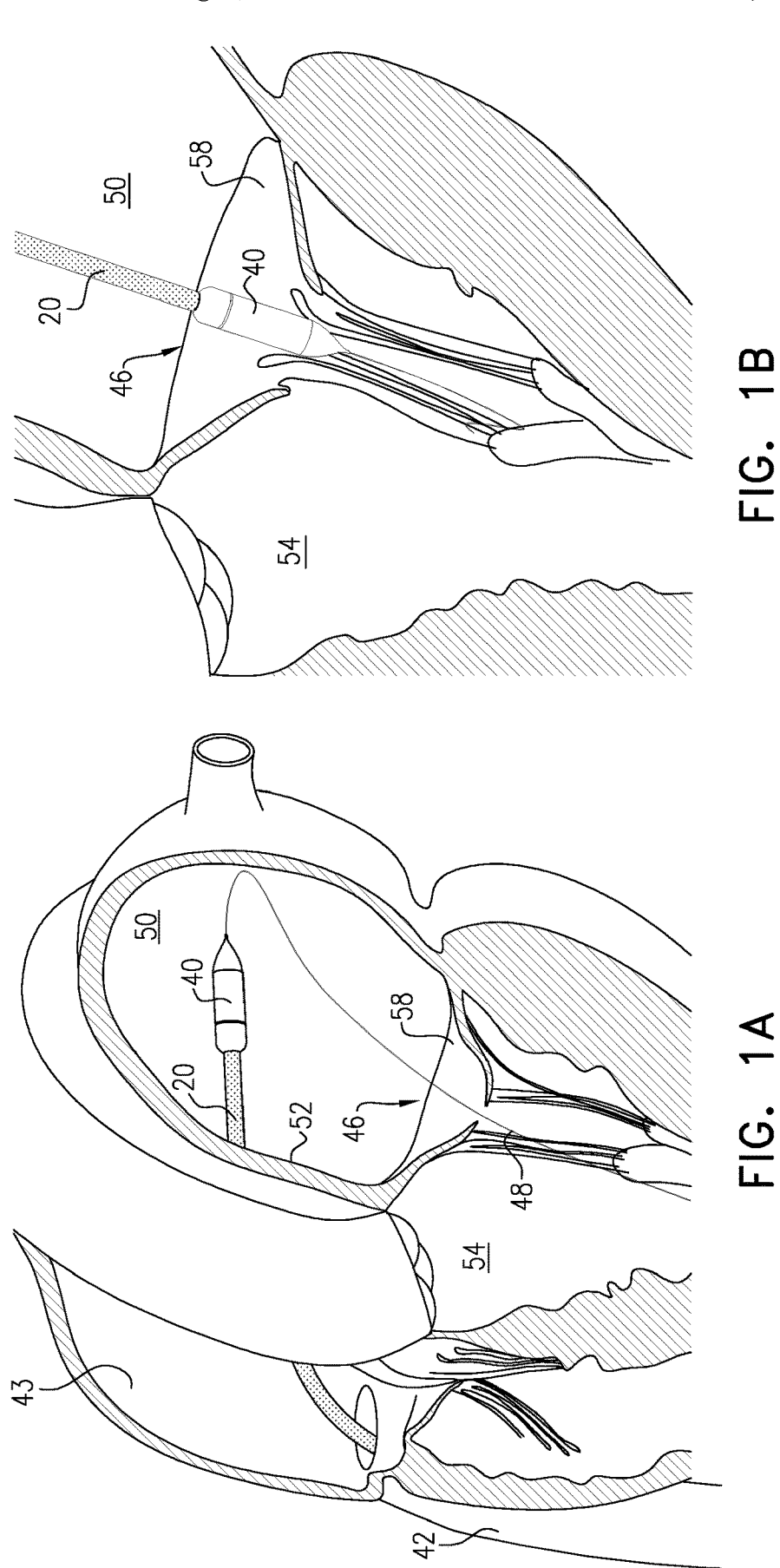
FIGS. 1A and 1B are schematic illustrations showing a delivery device being advanced toward a subject's left ventricle, in accordance with some applications of the present invention.
Figures 1C, 1D:
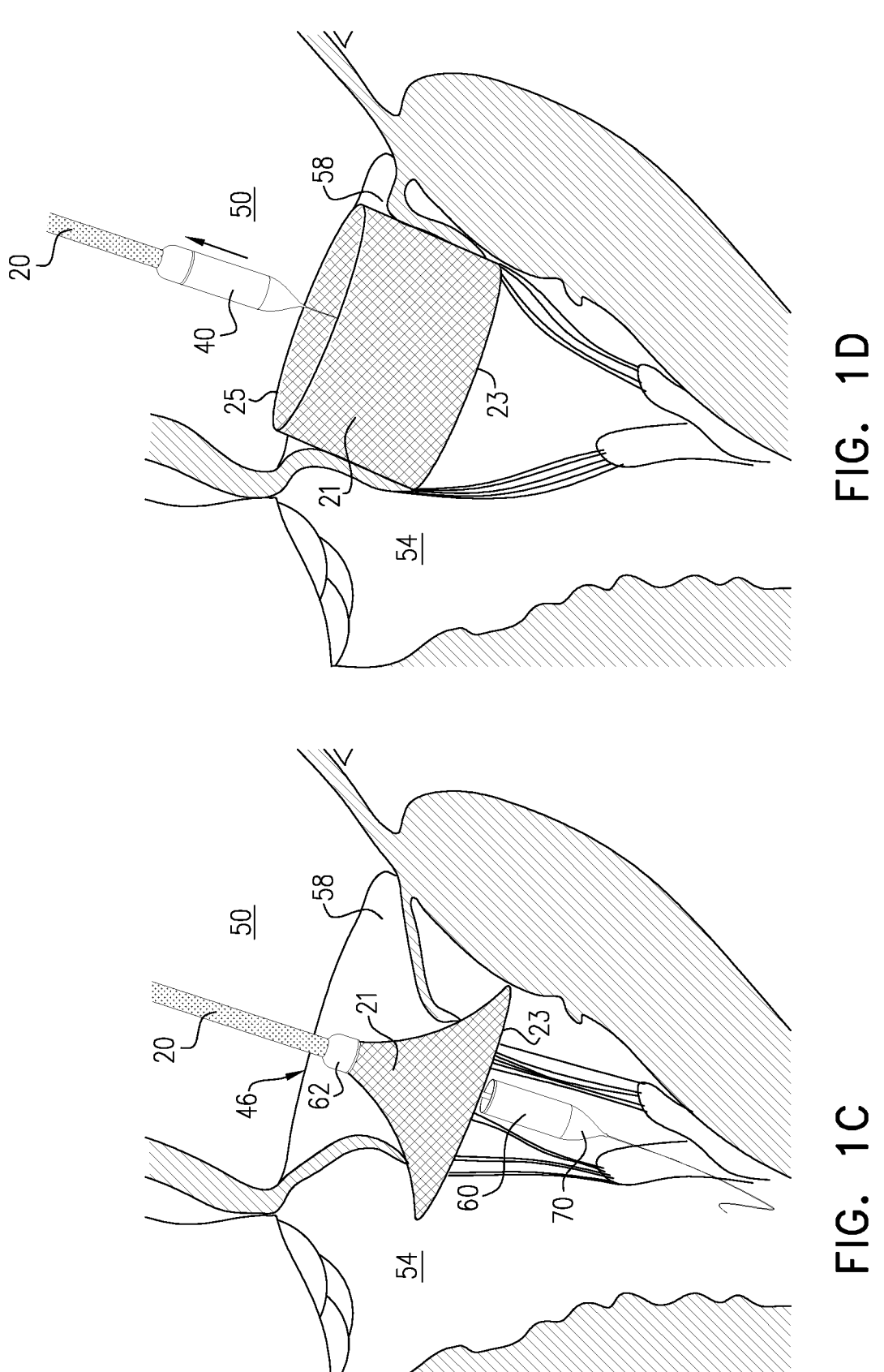
FIGS. 1C and 1D are schematic illustrations showing a percutaneously-implantable medical device being released from a capsule of the delivery device, in accordance with some applications of the present invention.

Reference is now made to FIGS. 1A and 1B, which are schematic illustrations showing the advancement of a delivery device 20 toward a subject's native mitral valve 46 and/or left ventricle 54, via a transseptal delivery approach, in accordance with some applications of the present invention. Reference is also made to FIGS. 1C and 1D, which are schematic illustrations showing a percutaneously-implantable medical device 21 being released from a capsule 40 of the delivery device, in accordance with some applications of the present invention. As shown in FIG. 1A, the distal end of delivery device 20 is typically advanced from the subject's vena cava 42 into the subject's right atrium 43, and from there into the subject's left atrium 50, via the interatrial septum 52. The distal end of the delivery device is advanced toward the native mitral valve, and is typically advanced through leaflets 58 of the native mitral valve and into left ventricle 54, as shown in FIG. 1B. For some applications, delivery device 20 is guided toward the subject's native mitral valve 46 over a guidewire 48. Typically, the delivery device is used to deliver percutaneously-implantable medical device 21, such as a prosthetic mitral valve (as shown schematically in FIGS. 1C and 1D), a mitral valve repair device (such as an annuloplasty ring or a mitral-leaflet clip), artificial chordae tendineae, and/or a different percutaneously-implantable medical device.

For some applications, the delivery device includes capsule 40 at its distal end. Typically, the percutaneously-implantable medical device is held in a crimped (i.e., radially-constrained) configuration inside the capsule, during delivery of the medical device to the subject's mitral valve and/or left ventricle. Further typically, in order to deploy the device at the subject's mitral valve and/or left ventricle, the medical device is released from the capsule, as described in further detail hereinbelow. For some applications, the medical device is a self-expandable medical device that is configured to self-expand radially upon being released from the capsule. For example, the medical device may include a shape-memory alloy (such as nitinol) that is shape set to a desired radially-expanded configuration. Alternatively or additionally, the device may actively be radially expanded after being released from the capsule (e.g., via balloon expansion). For some applications, a distal portion 23 of medical device 21 is first released from the capsule (as schematically illustrated in FIG. 1C), and a proximal portion 25 of the medical device is subsequently released from the capsule (as schematically illustrated in FIG. 1D), as described in further detail hereinbelow.

Figure 2A:
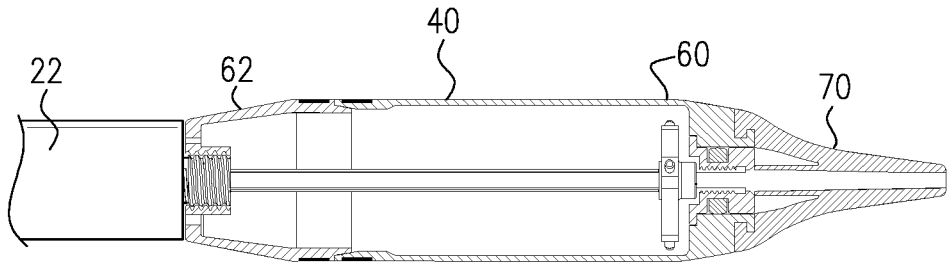
FIGS. 2A, 2B, and 2C are schematic illustrations of inner and outer steerable catheters of a delivery device, in accordance with some applications of the present invention.
Figure 2B:
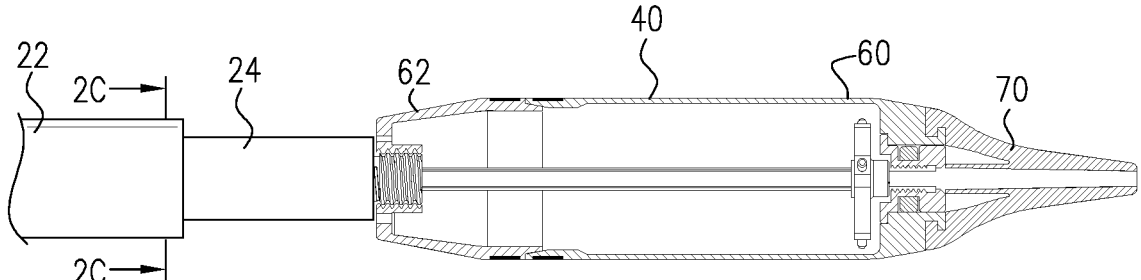
Figure 2C:
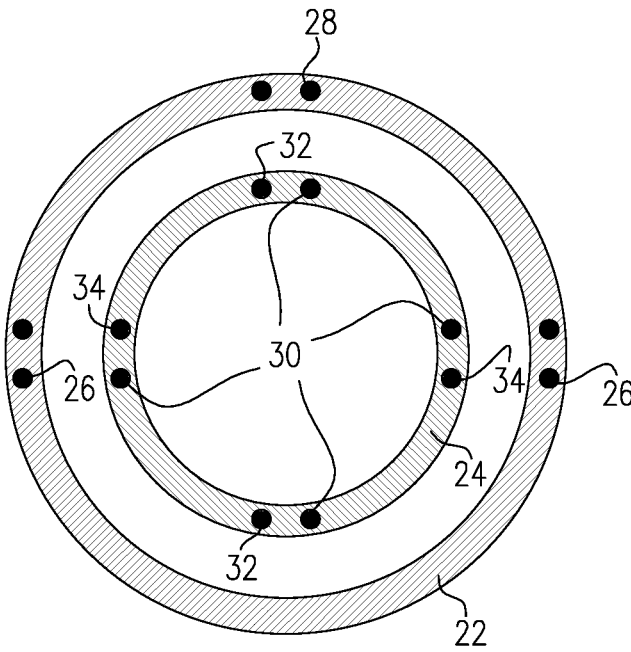

Reference is now made to FIGS. 2A, 2B, and 2C, which are schematic illustrations of an outer steerable catheter 22 and an inner steerable catheter 24 of delivery device 20, in accordance with some applications of the present invention. FIGS. 2A and 2B show side views and FIG. 2C shows a cross-sectional view of the outer and inner steerable catheters. As shown in the transition from FIG. 2A to FIG. 2B, typically the inner steerable catheter is axially-slidable with respect to the outer steerable catheter. Typically, during advancement of delivery device 20 from the subject's vena cava 42 into the subject's left atrium 50, via the interatrial septum 52 (anatomy shown in FIGS. 1A-B), the distal end of the inner steerable catheter is disposed inside the outer steerable catheter, as shown in FIG. 2A. Further typically, once the distal end of the outer steerable catheter is disposed inside the left atrium, the inner steerable catheter is advanced out of the distal end of the outer steerable catheter (i.e., the configuration shown in FIG. 2B) and then steered toward the subject's mitral valve and/or left ventricle. For some applications, the inner steerable catheter is configured to be steered independently of the outer steerable catheter once the inner steerable catheter has been advanced out of the distal end of the outer steerable catheter.

For some applications, the outer steerable catheter includes first and second steering deflection cables 26 that are configured to be operated by a user to steer the distal end of the outer catheter through a first outer-steerable-catheter deflection plane, toward the subject's interatrial septum. Alternatively (embodiment not shown), the outer catheter includes only a single steering-deflection cable 26 that is configured to be operated by a user to steer the distal end of the outer steerable catheter through the first outer-steerable-catheter deflection plane toward the subject's interatrial septum. Typically, in addition to one or more steering deflection cables 26, the outer catheter includes a height-adjustment deflection cable 28. Typically, the height-adjustment deflection cable 28 is configured to be operated by a user to deflect the distal end of the outer steerable catheter from within the left atrium toward the roof of the left atrium, by steering the tip of the outer steerable catheter through a second outer-steerable-catheter deflection plane. Typically, the second outer-steerable-catheter deflection plane is perpendicular to the first outer-steerable-catheter deflection plane. Accordingly, height-adjustment deflection cable 28 is typically disposed at a 90 degree angle with respect to steering-deflection cable(s) 26, as shown in FIG. 2C.

For some applications, steering deflection cables 26 are configured to steer the distal end of the outer steerable catheter through the first outer-steerable-catheter deflection plane through an angle of between 0 degrees and more than 60 degrees, or more than 75 degrees (e.g., 0-90 degrees). For some applications, height-adjustment deflection cable 28 is configured to steer the distal end of the outer steerable catheter through the second outer-steerable-catheter deflection plane through an angle of between 0 degrees and more than 30 degrees, or more than 40 degrees (e.g., 0-45 degrees), to deflect the distal end of the outer steerable catheter from within the left atrium toward the roof of the left atrium.

It is noted that in FIG. 2C, each steering deflection cable is shown as being doubled. This is because, typically, each steering deflection cable follows a first path from a proximal end of the catheter to the distal end of the catheter, before following a return path from the distal end of the catheter to the proximal end of the catheter.

It is noted that within the left atrium, the inner steerable catheter typically needs to maneuver through a curve of approximately 90 degrees. This is because the inner steerable catheter is advanced out of the outer steerable catheter after the outer steerable catheter has penetrated the interatrial septum. Thus, the tip of the inner steerable catheter typically advances from the outer steerable catheter facing a lateral direction and must be steered to face an inferior-anterior direction in order to advance toward the mitral valve. Typically, the outer steerable catheter is made to penetrate the interatrial septum below the roof of the atrium, as shown in FIGS. 1A-B (e.g., at a posterior-inferior, or a posterior-superior location), since the septum is thinner and more easily penetrated at this location. As described above, the height-adjustment deflection cable 28 is configured to be operated by a user to deflect the distal end of the outer steerable catheter from within the left atrium toward the roof of the left atrium. Typically, this provides the inner steerable catheter with a greater height within which to maneuver through the above-described curve, such that the curve is less acute, and also provide height for the capsule to deploy above the annulus.

Typically, inner steerable catheter 22 includes one or more steering deflection cables 30. For some applications, the inner steerable catheter includes (a) a first set 32 of one or more (e.g., a pair of) steering deflection cables that are configured to be operated by a user to steer the distal end of the inner steerable catheter through a first inner-steerable-catheter deflection plane, toward the subject's mitral valve, and (b) a second set 34 of one or more (e.g., a pair of) steering deflection cables that are configured to be operated by a user to steer the distal end of the inner steerable catheter through a second inner-steerable-catheter deflection plane, such as to align the distal end of the inner steerable catheter with the subject's mitral valve.

For some applications, first set 32 of steering deflection cables is configured to steer the distal end of the inner steerable catheter through the first inner-steerable-catheter deflection plane through an angle of between 0 degrees and more than 80 degrees, or more than 100 degrees (e.g., 120 degrees). For some applications, second set 34 of steering deflection cables is configured to steer the distal end of the inner steerable catheter through the second inner-steerable-catheter deflection plane through an angle of at least between −45 degrees and +45 degrees, such as to align the distal end of the inner steerable catheter with the subject's mitral valve. Typically, set 32 of steering deflection cable(s) 28 is disposed at a 90 degree angle with respect to second set 34 of steering deflection cable(s), as shown in FIG. 2C.

It is noted that although FIGS. 2A-C show the use of inner steerable catheter 24 within outer steerable catheter 22, for some applications, a steerable catheter that is configured like outer steerable catheter 22 is used in the absence of an inner steerable catheter. For example, a medical device may be steered directly from within a steerable catheter that is configured like outer steerable catheter 22, toward the subject's mitral valve and/or left ventricle. Similarly, although outer steerable catheter 22 is shown as including two steering deflection cables 26, the scope of the present invention includes an outer steerable catheter that includes only a single steering deflection cable 26 in combination with height-adjustment deflection cable 28. In addition, although inner steerable catheter 24 is shown as including two sets 32 and 34 of steering deflection cables 30, the scope of the present invention includes an inner steerable catheter that includes only a single set of, or even a single steering deflection cable 30.

Figures 3A, 3B:
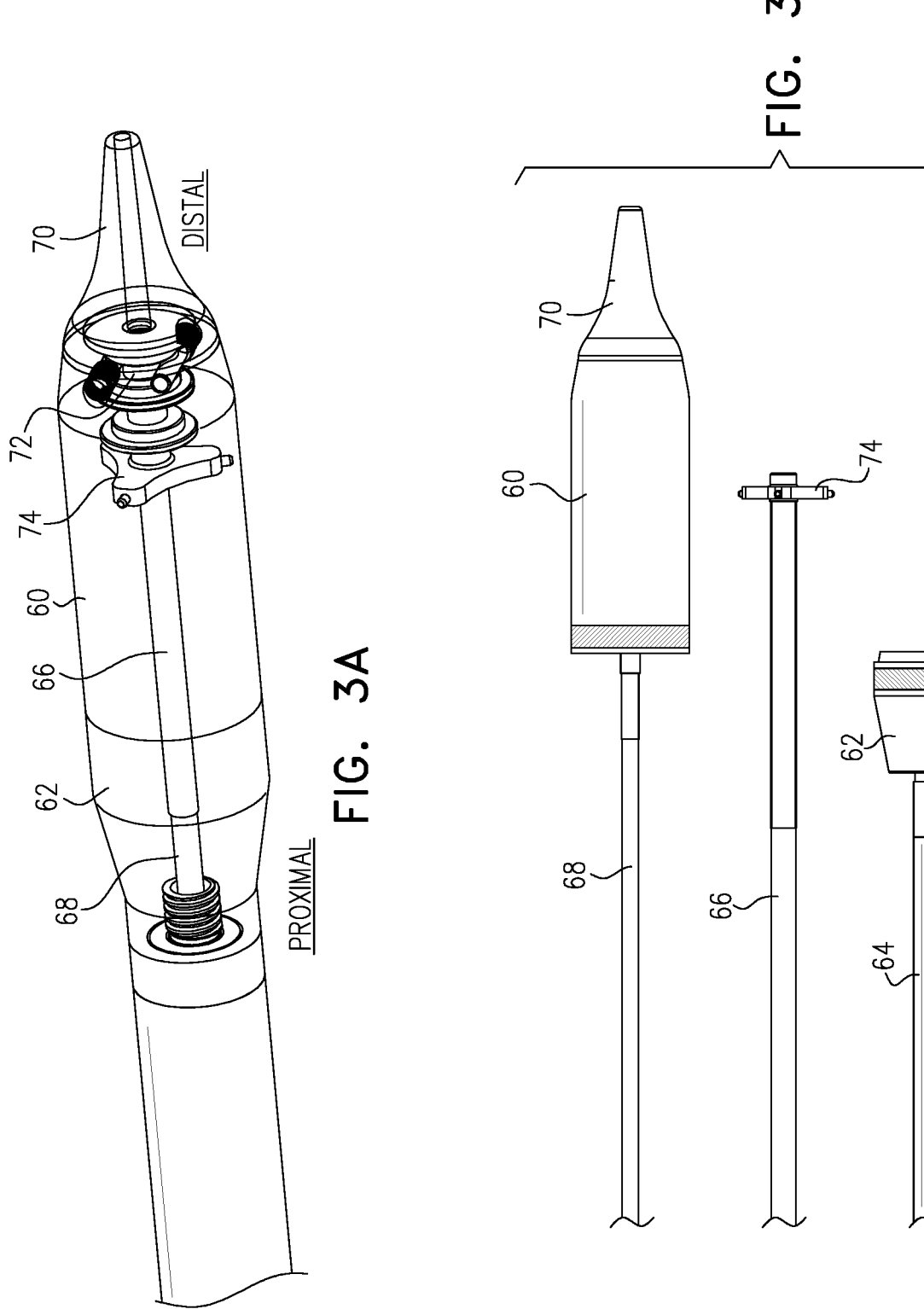
FIGS. 3A and 3B are schematic illustrations showing a capsule of a delivery device, in accordance with some applications of the present invention.

Reference is now made to FIGS. 3A and 3B, which are schematic illustrations showing capsule 40 of delivery device 20, in accordance with some applications of the present invention. Typically, the medical device is held in a crimped (i.e., radially-constrained) configuration inside the capsule, during delivery of the medical device to a deployment location (such as the subject's mitral valve and/or left ventricle). Further typically, in order to deploy the device at the deployment location, the medical device is released from the capsule. It is noted that a capsule as shown in FIGS. 3A-B (as well as in FIGS. 4A-C) may be used with any medical device that is delivered to deployment location within a subject's body in a crimped configuration and is not limited to being used with devices that are deployed within the mitral valve and/or left ventricle. For example, a capsule as shown in FIGS. 3A-B (as well as in FIGS. 4A-C) could be used with a medical device that is delivered to a subject's aorta, vena cava tricuspid valve, right ventricle, right atrium, right ventricle, pulmonary vein, pulmonary artery, etc.

For some applications, the capsule includes a distal capsule portion 60 configured to maintain a distal portion of the medical device in the radially-constrained configuration during delivery of the medical device to the deployment location, and a proximal capsule portion 62 configured to maintain a proximal portion of the medical device in a radially-constrained configuration during delivery of the medical device to the deployment location. Typically, the proximal and distal portions are reversibly couplable to each other, as described in further detail hereinbelow. For some applications, the capsule additionally includes a tapered distal tip 70 that is configured to facilitate advancement of the capsule into the subject's vasculature, and, subsequently, acts as a dilator to advance through the interatrial septum. Typically, the distal tip is made of a soft material, such that the tip is atraumatic and does not cause injury to tissue of the subject during advancement of the delivery device to the deployment location. The distal tip typically allows the advancement of the system on a guidewire and its soft material complies with the guidewire direction.

For some applications, an outer shaft 64, a medial shaft 66, and an inner shaft 68 are all disposed within inner steerable catheter 24 (shown in FIGS. 2B-C). The outer shaft is typically coupled to proximal capsule portion 62, such that axial motion of the outer shaft relative to the medial shaft and the inner shaft transmits axial motion to the proximal capsule portion relative to the medial shaft and the inner shaft. In order to release the proximal portion of the medical device from within the proximal capsule portion, the outer shaft is typically retracted axially, proximally relative to the medial shaft and the inner shaft, which causes the proximal capsule portion to be retracted from over the proximal portion of the medical device. (It is noted that, rather than retracting the outer shaft, the relative proximal motion of the outer shaft with respect to the medial shaft and the inner shaft may be effected by advancing the medial shaft and the inner shaft distally relative to the outer shaft.)

Inner shaft 68 is typically coupled to the distal capsule portion 60 such that that axial motion of the inner shaft transmits axial motion to the distal capsule portion. (It is noted that rotational motion of the distal capsule portion is typically separated from rotational motion of the inner shaft via a bearing mechanism 72, as described in further detail hereinbelow with reference to FIGS. 4A-C.) For some applications, the delivery device includes a distal device interface 74, which is configured to secure a distal portion of the medical device at a fixed axial location with respect to the medial shaft, so long as the distal portion of the medical device is held within the distal capsule portion. For some applications, the distal device interface is a flange which extends radially from the medial shaft, as shown. In order to release the distal portion of the medical device from within the distal capsule portion, the inner shaft is typically advanced axially and distally (typically using the techniques described hereinbelow with reference to FIGS. 4A-C) relative to the medial shaft. This causes the distal capsule portion to be advanced distally relative to the distal device interface. Once the proximal end of the distal capsule portion is advanced beyond the distal device interface, the distal portion of the medical device is typically released from the distal device interface (typically, via radial self-expansion of the distal portion of the medical device, and/or by another mechanism as described hereinabove).

Figure 4A:
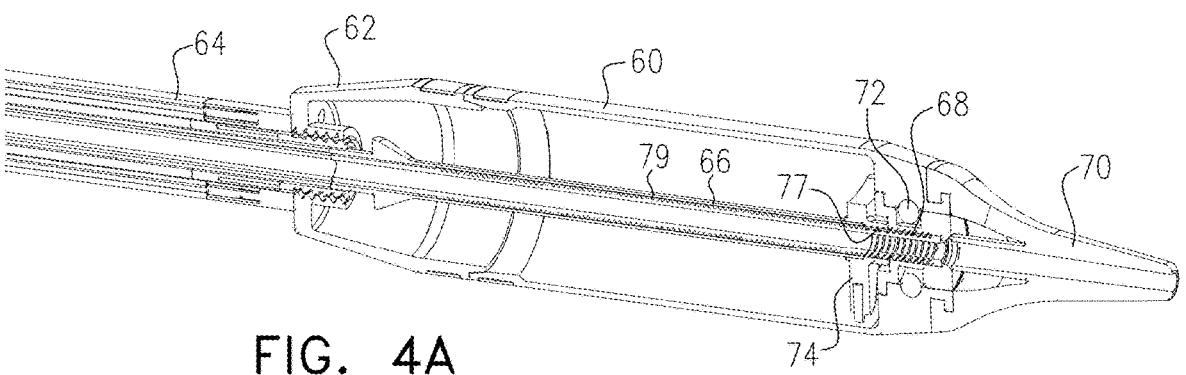
FIGS. 4A, 4B, and 4C are schematic illustrations of proximal and distal capsule portions of the delivery device, in accordance with some applications of the present invention.
Figure 4B:
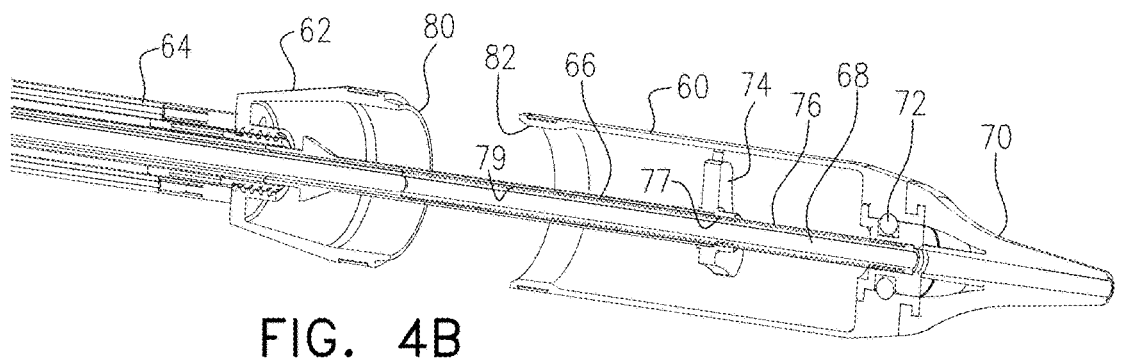
Figure 4C:
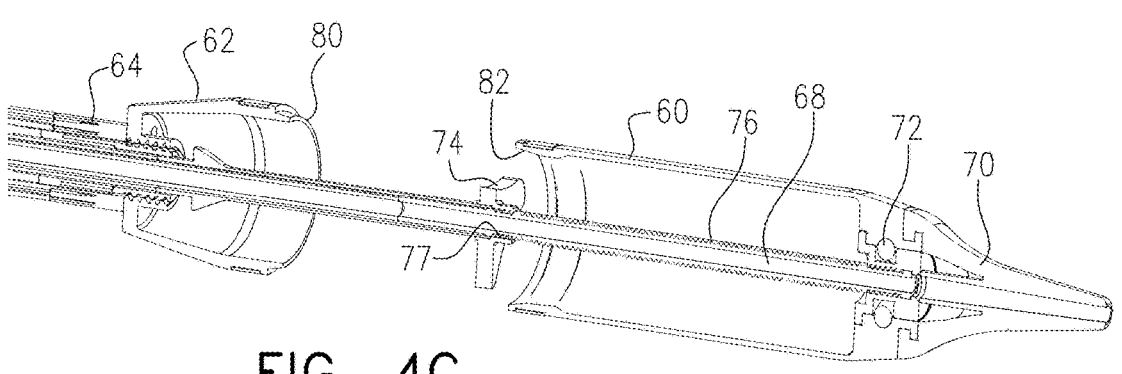

Reference is now made to FIGS. 4A, 4B, and 4C, which are schematic illustrations of proximal capsule portion 62 and distal capsule portion 60 of the delivery device at respective stages of the advancement of distal capsule portion 60 with respect to proximal capsule portion 62, in accordance with some applications of the present invention. In some cases, it is desirable to advance the distal capsule portion 60 with respect to proximal capsule portion 62 in a precisely controlled manner. For example, when used with a prosthetic mitral valve frame as described in US 2022/0015896 to Agian (which is incorporated herein by reference), it may be desirable to initially release an intermediate portion of the valve frame (e.g., radially-expandable arms of the valve frame) from being covered by the distal capsule portion, without fully releasing the entire distal portion of the valve frame. Typically, in order to allow a physician to maintain precise control of the advancement of distal capsule portion 60 with respect to proximal capsule portion 62, the physician uses a rotational control mechanism (e.g., mechanism 108 shown in FIG. 5) and the rotational motion of the rotational control mechanism is converted to axial motion of inner shaft 68 (which is coupled to the distal capsule portion). For some such applications, the conversion of the rotational motion to the axial motion of inner shaft 68 is effected at the distal end of the inner shaft, and typically within the capsule. It is noted that if the conversion of the rotational motion to the axial motion of inner shaft 68 were to be effected at the proximal end of the inner shaft, the axial motion of the inner shaft would then need to be transmitted along the entire length of the inner shaft before being transmitted to the distal capsule portion, which can result in imprecise transmission of axial motion to the distal capsule portion. By contrast, by converting the rotational motion to the axial motion of inner shaft 68 at the distal end of the inner shaft (in accordance with some applications of the present invention), the axial motion does not need to be transmitted along the entire length of the inner shaft before being transmitted to the distal capsule portion. Rather, the axial motion is transmitted from within the capsule to the distal capsule portion.

For some applications, inner shaft 68 defines a threaded outer surface 76 at its distal end (threaded outer surface 76 functioning as a screw), and an inner surface 77 of distal device interface 74 (which is described hereinabove is typically a flange) and/or an inner surface 79 of medial shaft 66 is correspondingly threaded. The threaded inner surface of distal device interface 74 and/or medial shaft 66 acts as a nut, such that rotation of the distal end of the inner shaft causes the inner shaft to advance distally with respect to the distal device interface 74. As described hereinabove, typically the distal device interface 74 secures the distal end of the medical device and further typically, axial motion of the inner shaft is transmitted to the distal capsule portion. Therefore, the advancement of the inner shaft with respect to the distal device interface 74 causes the distal capsule portion to advance relative to a distal end of the medical device. As described hereinabove, for some applications, the distal capsule portion includes a bearing mechanism 72. The bearing mechanism is configured to separate rotational motion of the distal capsule portion from rotational motion of the inner shaft. Thus, rotation of the inner shaft causes the distal capsule portion to be advanced distally relative to the distal end of the medical device, but without causing the distal capsule portion to rotate.

It is noted that the scope of the present application generally includes any capsule configured to house the medical device during delivery of the medical device to the deployment location and configured to maintain the medical device in a radially-constrained configuration during delivery of the medical device to the deployment location. A handle includes a rotational control mechanism (e.g., mechanism 108) that is configured to transmit rotational motion to the capsule. A nut (e.g., threaded inner surface of distal device interface 74 and/or medial shaft 66) that comprises a part of a screw-and-nut mechanism is disposed within the capsule, and is configured to convert the rotational motion to axial motion of a portion of the capsule, to thereby release at least a portion of the medical device from within the capsule. For example, the capsule may include a single-piece capsule with the nut (e.g., threaded inner surface of distal device interface 74 and/or medial shaft 66) being disposed at one end of the capsule (e.g., the proximal end or the distal end), such that in response to the rotational motion, the entire capsule moves axially.

Typically, once the medical device has been released from within capsule 40, the proximal and distal portions of the capsule are re-coupled to each other before being retracted from within the subject's body. For some applications, the capsule includes a guide portion defined by at least one of the distal and proximal capsule portions. The guide portion is configured to guide the distal and proximal capsule portions back into their coupled configuration, subsequent to the medical device having been deployed. For example, as shown in FIG. 4B-C, for some applications the proximal capsule portion defines a lip 80 at its distal end, and the distal capsule portion defines a corresponding lip 82 at is proximal end, with lips 80 and 82 being shaped such as to slide into place with respect to each other. Alternatively, only one of the capsule portions defines a lip, and the lip is configured to receive the other capsule portion (embodiment not shown). Typically, when the proximal and distal portions are correctly coupled to each other they are shaped such as to define a substantially smooth outer surface. In this manner, during advancement of the capsule to the medical device deployment location, the capsule is atraumatic and does not cause damage to tissue of the subject. Similarly, during retraction of the capsule from the medical device deployment location, the capsule is atraumatic and does not cause damage to tissue of the subject or to the deployed medical device. For some applications, the above-mentioned lip is formed as a complete ring (as shown). For some applications (not shown), a lip that is generally as described above is split into multiple, separate, arc-shaped, segments. For example, the lip may be formed from 4 arc-shaped segments, spaced 90 degrees apart from each other and each covering an arc of 30 degrees. In this way the medical device may be released before the entire capsule is removed, hence saving on the height that is required to release the medical device.

Figure 5:
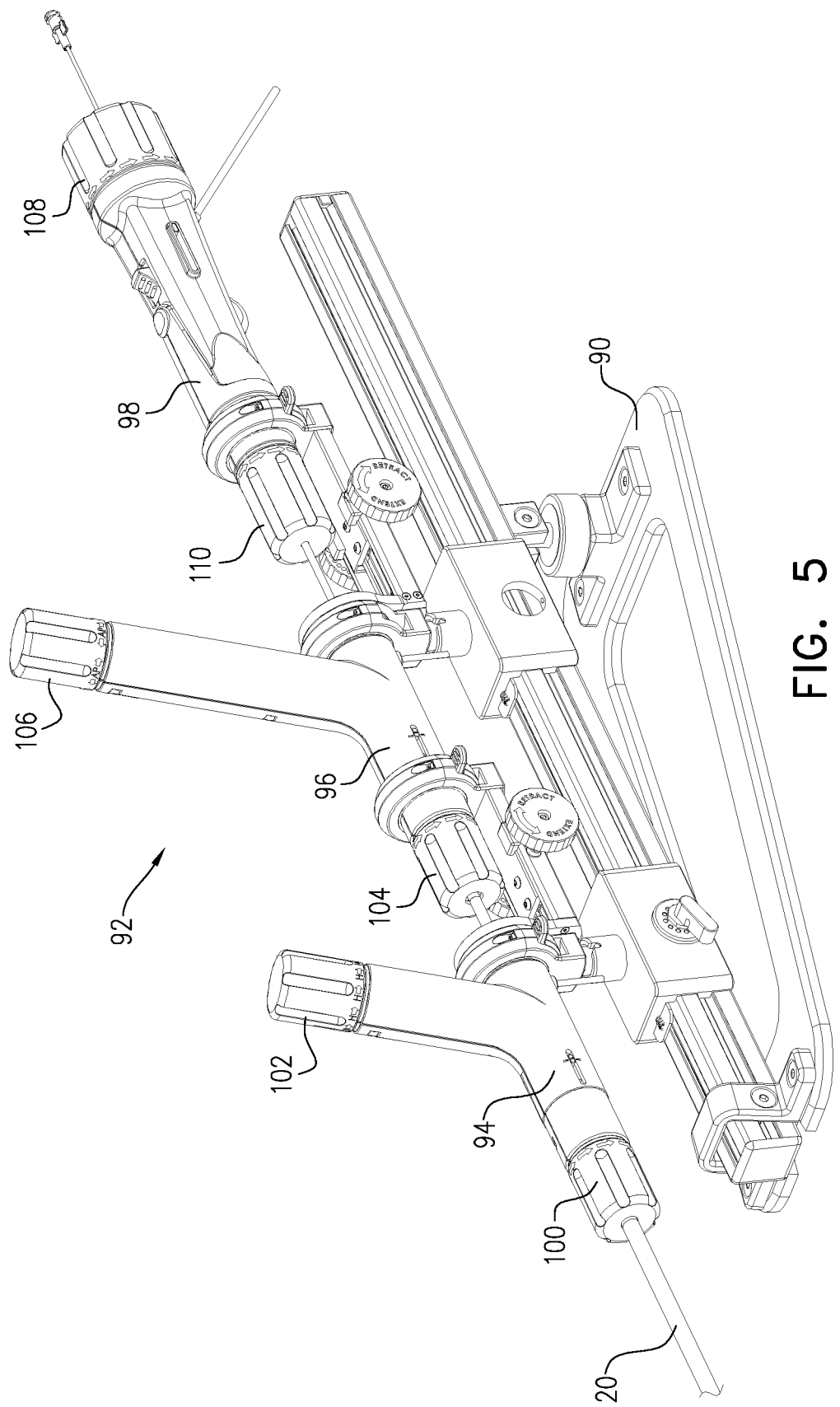
FIG. 5 is a schematic illustration of a stage and handle portion of the delivery device, in accordance with some applications of the present invention.

FIG. 5 is a schematic illustration of a stage 90 and handle portion 92 of the delivery device, in accordance with some applications of the present invention. For some applications, the handle portion include a first handle 94 configured to control steering of outer steerable catheter 22, a second handle 96 configured to control steering of inner steerable catheter 24, and a deployment handle 98 configured to control the release of the medical device from capsule 40.

Typically, first handle 94 includes a first rotational control mechanism 100 for controlling steering deflection cables 26 (which are configured to be operated by a user to steer the distal end of the outer steerable catheter through a first outer-steerable-catheter deflection plane toward the subject's interatrial septum). Further typically, first handle 94 includes a second rotational control mechanism 102 for controlling height-adjustment deflection cable 28 (which is configured to be operated by a user to deflect the distal end of the outer steerable catheter from within the left atrium toward the roof of the left atrium, by steering the tip of the outer steerable catheter through a second outer-steerable-catheter deflection plane).

Typically, second handle 96 includes a first rotational control mechanism 104 for controlling first set 32 of steering deflection cables (which are configured to be operated by a user to steer the distal end of the inner steerable catheter through a first inner-steerable-catheter deflection plane, toward the subject's mitral valve). Further typically, second handle 96 includes a second rotational control mechanism 106 for controlling second set 34 of steering deflection cables (which are configured to be operated by a user to steer the distal end of the inner steerable catheter through a second inner-steerable-catheter deflection plane, such as to align the distal end of the inner steerable catheter with the subject's mitral valve).

As described hereinabove, the deployment handle typically includes a rotational control mechanism 108 for controlling axial motion of the distal capsule portion 60. Further typically, the deployment handle includes a second rotational control mechanism 110 for controlling axial motion of proximal capsule portion 62. Typically, the handle portion includes a plurality of flushing ports, via which respective catheter and shafts are flushed.

Typically, stage 90 is configured to position handle portion 92 and allows adjustments of position of the handle portion. For some applications, the stage is configured to facilitate quick attachment of the handle portion to the stage without requiring any screws, e.g., via a snap-lock mechanism. For some applications, the stage is configured to facilitate modification of the orientation of the handle portion during the procedure to allow realignment of the handle portion with respect to the percutaneous access point.

Figures 6A, 6B:
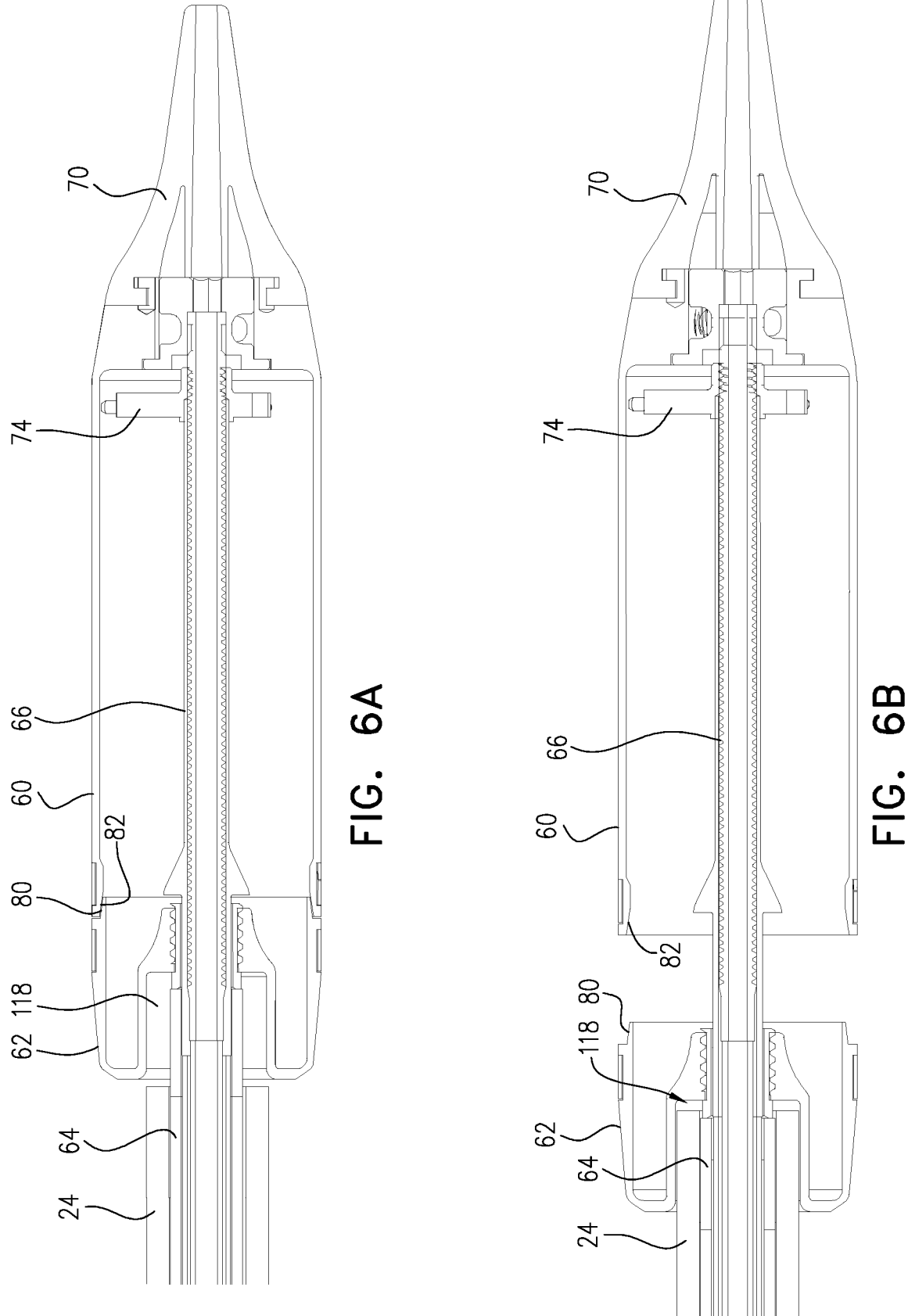
FIGS. 6A and 6B are schematic illustrations of a delivery device, in accordance with some applications of the present invention.

Reference is now made to FIGS. 6A and 6B, which are schematic illustrations of delivery device 20, in accordance with some applications of the present invention. In general, delivery device 20 as shown in FIGS. 6A and 6B is similar to that shown in FIGS. 1A-5, except for the differences described hereinbelow. For some applications, the proximal end of proximal capsule portion 62 defines a recess 118. Typically, the recess is sized such that, as the proximal capsule portion is retracted, proximal capsule portion is able to overlap with a distal end of a delivery catheter (e.g., inner steerable catheter 24 of delivery device 20, described hereinabove with reference to FIGS. 2A-C.) Typically, if not for the recess, it would be necessary for there to be a gap between the distal end of the delivery catheter and the proximal capsule portion, in order to enable the proximal capsule portion to be retracted relative to the delivery catheter (e.g., in order to release the proximal end of the implantable device). By contrast, when the proximal capsule portion includes recess 118, the proximal capsule portion is typically disposed adjacent to distal end of the delivery catheter even before the proximal capsule portion is retracted (as shown in FIG. 6A). Alternatively, the proximal capsule portion partially overlaps with the distal end of the delivery catheter even before the proximal capsule portion is retracted (embodiment not shown). Subsequently, when the proximal capsule portion 62 is retracted, the proximal end of the proximal capsule portion is made to overlap (or to further overlap) with distal end of the delivery catheter, by the recess sliding over the distal end of the delivery catheter. Typically, recess 118 allows the device to occupy less space (e.g., less height) within the left atrium than would otherwise be required, by removing the need for there to be a gap between the distal end of the delivery catheter and the proximal capsule portion.

Figures 7, 8:
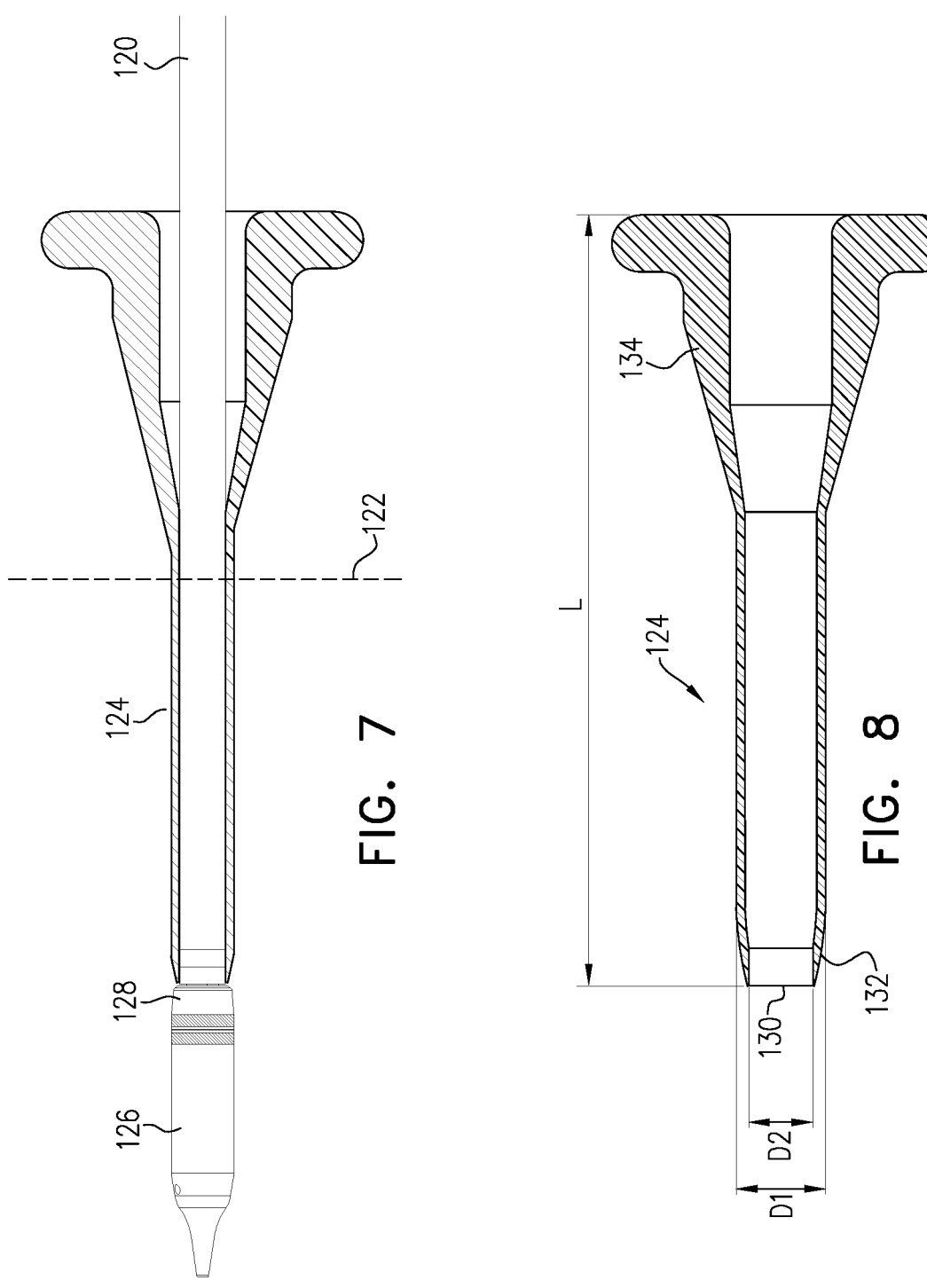
FIG. 7 is a schematic illustration of a delivery device being inserted percutaneously into a subject's body via a percutaneous introducer sheath, in accordance with some applications of the present invention.
FIG. 8 is a schematic illustration of a percutaneous introducer sheath, in accordance with some applications of the present invention.

Reference is now made to FIG. 7 which is a schematic illustration of a delivery device 120 being inserted percutaneously into a subject's body through a puncture in the patient's skin 122 via a percutaneous introducer sheath 124, in accordance with some applications of the present invention. Typically, the delivery device is used to deliver a medical device (e.g., medical device 21 shown in FIGS. 1C-D) in a minimally-invasive procedure, in which the medical device is inserted percutaneously (through a puncture in the skin) to a deployment location at which the device is to be deployed. Many such medical devices are deployed within the subject's vasculature and/or within the subject's heart, via a puncture in the subject's vasculature. For example, such medical devices may include prosthetic valves (e.g., a prosthetic mitral valve, a prosthetic aortic valve, and/or a prosthetic tricuspid valve), valve repair devices (e.g., an annuloplasty ring or an edge-to-edge device, such as a mitral-leaflet clip), stents, hole-closure devices, and/or intravascular simulation devices. Typically, depending on the deployment location, larger medical devices are inserted into the subject's vasculature via the femoral vein or the femoral artery, while smaller devices are inserted via the radial vein or the radial artery, or another vein or artery. Typically, the delivery device is inserted through the puncture in the patient's skin and the puncture in the patient's vasculature via the percutaneous introducer sheath. For some applications, delivery device 20 (described hereinabove with reference to FIGS. 1A-6B) is used as delivery device 120.

During delivery of the medical devices to the deployment location, the medical devices are typically maintained in a radially-constrained (i.e., crimped) configuration within the delivery device. The medical devices are radially expanded to their deployment configurations when disposed at the deployment location. In some cases, the medical devices are configured to self-expand, while in other cases the medical devices are radially expanded in an active manner, e.g., via balloon expansion.

For some applications, the delivery device includes a capsule 126 at its distal end, and the capsule is configured to house the medical device in its radially-constrained (i.e., crimped) configuration during delivery of the medical device to deployment location. For some such applications, the capsule is greater in diameter than a portion 128 of the delivery device that is proximal to the capsule. (As noted above, for some applications, delivery device 20 (described hereinabove with reference to FIGS. 1A-6B) is used as delivery device 120, in which case capsule 126 typically corresponds to capsule 40 and portion 128 typically corresponds to steerable outer catheter 22.) In some cases, the difference in the width between the capsule and the portion of the delivery device that is proximal to the capsule can give rise to bleeding after the capsule has been advanced through the vascular puncture. This is because the vascular puncture is widened by the insertion of the capsule, such that the vascular walls surrounding the puncture do not seal against the portion of the delivery device that is proximal to the capsule and narrower than the capsule. Such problems may also arise with other forms of delivery devices having a widened distal portion and a proximal portion that is narrower than the widened distal portion. The scope of the present application is applicable to all such delivery devices, mutatis mutandis.

In accordance with some applications of the present invention, the percutaneous introducer sheath is made of a stretchable material (e.g., an elastomer, such as silicone, or polyurethane). As described in further detail hereinbelow, the percutaneous introducer sheath defines a lumen 130, which in the non-stretched state of the percutaneous introducer sheath is sized such as to accommodate the portion of the delivery device that is proximal to the capsule. Further typically, in the non-stretched state of the percutaneous introducer sheath, the outer diameter of the sheath is approximately equal to (or equal to) or greater than the outer diameter of the capsule. For some applications, any difference between the outer diameter of the outer diameter of the percutaneous introducer sheath and the outer diameter of the capsule is less than 20 percent (e.g., less than 5 percent, or less than 2 percent) of the outer diameter of the capsule. Before inserting the percutaneous introducer sheath into the subject's body, the capsule is typically advanced through lumen 130 by stretching the percutaneous introducer sheath, such that the entire capsule is disposed distally of the distal end of the percutaneous introducer sheath (e.g., as shown in FIG. 7). The capsule is then advanced through the subject's skin and into the subject's vasculature, followed by the percutaneous introducer sheath. Typically, even after the vascular puncture has been widened by the capsule, the vascular walls surrounding the puncture seal against the outside of the percutaneous introducer sheath, since the outer diameter of the sheath is approximately equal to the outer diameter of the capsule. For some applications, during the advancement of the delivery device through the subject's vasculature, the percutaneous introducer sheath is disposed such that it remains within the punctures in the subject's skin and vasculature, and the portion 128 of the delivery device that is proximal to the capsule is advanced through lumen 130.

It is noted that, by virtue of the introducer sheath being stretchable, the introducer sheath can be loaded onto the delivery device in the setting in which the procedure takes place (e.g., in the catheterization laboratory). As described above, within this setting and before inserting the percutaneous introducer sheath into the subject's body, the capsule is typically advanced through lumen 130 by stretching the percutaneous introducer sheath, such that the entire capsule is disposed distally of the distal end of the percutaneous introducer sheath. By contrast, if the introducer sheath were not sufficiently stretchable, the introducer sheath would have to be placed around portion 128 of the delivery device in a clean room, prior to the procedure, as part of the assembly process of the delivery device (or a capsule having a smaller diameter would be required).

Reference is now made to FIG. 8, which is a schematic illustration of percutaneous introducer sheath 124, in accordance with some applications of the present invention. For some applications, the introducer sheath is a femoral introducer sheath and has a total length L of between 60 and 120 mm, e.g., between 70 and 110 mm. Typically, at its distal end the femoral introducer sheath has an outer diameter D1 of between 8 mm and 12 mm, e.g., approximately 10 mm. For some applications, the diameter D2 of lumen 130 defined by the introducer sheath is between 7 and 10 mm, e.g., approximately 8 mm, or approximately 9 mm. Typically, the smaller the diameter of the lumen, the harder it is to insert the capsule through the lumen and, subsequently to advance the delivery device through the lumen. For some applications, the lumen is lubricated with a lubricant (e.g., steric oil) before and/or during the procedure. For some applications (not shown), the introducer sheath includes a flushing port to facilitate flushing of the introducer sheath with the lubricant.

For some applications, a distal portion 132 of the introducer sheath is tapered, typically with both the outer diameter of the sheath and the diameter of the lumen narrowing within the distal portion. The tapering of the distal portion of the introducer sheath typically enhances sealing between the introducer sheath and the delivery device. In particular, the narrowing of the lumen within the distal portion typically creates a seal between the introducer sheath and the delivery device. For some applications, as a result of the formation of this seal, there is no need to provide forward flushing of the space between the introducer sheath and the delivery device. Typically, the proximal end of the introducer sheath includes a widened portion 134 to facilitate holding the introducer sheath in place by a medical professional. For some applications, the widened portion allows the medical professional to pull and push the introducer sheath during the procedure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a medical device, comprising:

a delivery device configured to deliver the medical device to a mitral valve and/or a left ventricle of a subject, the delivery device comprising a steerable catheter that comprises:

an outer steerable catheter;

an inner steerable catheter that is disposed within the outer steerable catheter and a distal portion of which is configured to be advanceable out of a distal end of the outer steerable catheter and to be steered independently of the outer steerable catheter; and a capsule configured to house the medical device during delivery of the medical device to the mitral valve and/or the left ventricle, the capsule comprising:

a distal capsule portion configured to maintain a distal portion of the medical device in a radially-constrained configuration during delivery of the medical device to the mitral valve and/or the left ventricle; and a proximal capsule portion configured to maintain a proximal portion of the medical device in a radially-constrained configuration during delivery of the medical device to the mitral valve and/or the left ventricle, wherein a proximal capsule portion defines a recess, such that the proximal end of the proximal capsule portion is configured to be retracted such as to overlap with a distal end of the inner steerable catheter.

2. The apparatus according to claim 1, wherein the a-steerable catheter comprising comprises two or more deflection cables, at least one of the deflection cables being a steering deflection cable configured to steer a distal portion of the steerable catheter from a vena cava of the subject through a right atrium and an interatrial septum of the subject and into a left atrium of the subject, by steering the distal portion of the steerable catheter through a first steerable-catheter deflection plane, and at least one of the deflection cables being a height-adjustment deflection cable configured to deflect a tip of the steerable catheter relative to a portion of the steerable catheter that is proximal to the tip, such that the tip is deflected from within the left atrium toward a roof of the left atrium, by steering the tip of the steerable catheter through a second steerable-catheter deflection plane.

3. The apparatus according to claim 2, wherein the height-adjustment deflection cable is disposed at a 90 degree angle with respect to the steering deflection cable.

4. The apparatus according to claim 2, wherein the steering deflection cable is configured to steer the distal portion of the steerable catheter through the first steerable-catheter deflection plane through an angle of between 0 degrees and more than 60 degrees, to steer the distal portion of the steerable catheter from the vena cava through the right atrium and the interatrial septum of the subject and into the left atrium of the subject.

5. The apparatus according to claim 2, wherein the height-adjustment deflection cable is configured to steer the tip of the steerable catheter through the second steerable-catheter deflection plane through an angle of more than 30 degrees, to deflect the tip of the steerable catheter relative to the portion of the steerable catheter that is proximal to the tip.

6. The apparatus according to claim 2, wherein the inner steerable catheter comprises a first set of one or more steering deflection cables that are configured to steer a distal end of the inner steerable catheter through a first inner-steerable-catheter deflection plane toward the subject's mitral valve, and a second set of one or more steering deflection cables that are configured to steer the distal end of the inner steerable catheter through a second inner-steerable-catheter deflection plane, such as to align the distal end of the inner steerable catheter with the subject's mitral valve.

7. The apparatus according to claim 6, wherein the first set of one or more steering deflection cables are configured to steer the distal end of the inner steerable catheter through the first inner-steerable-catheter deflection plane through an angle of more than 80 degrees, to steer the distal end of the inner steerable catheter toward the subject's mitral valve.

8. The apparatus according to claim 6, wherein the second set of one or more steering deflection cables are configured to steer the distal end of the inner steerable catheter through the second inner-steerable-catheter deflection plane through an angle of at least between −45 degrees and +45 degrees, to align the distal end of the inner steerable catheter with the subject's mitral valve.

9. The apparatus according to claim 6, wherein the first set of one or more steering deflection cables is disposed at a 90 degree angle with respect to the second set of one or more steering deflection cables.

10. An apparatus for use with a medical device comprising:

a delivery device configured to deliver the medical device to a deployment location within a body of a subject, the delivery device comprising:

a delivery catheter; and a capsule configured to house the medical device during delivery of the medical device to the deployment location, the capsule comprising:

a distal capsule portion configured to maintain a distal portion of the medical device in a radially-constrained configuration during delivery of the medical device to the deployment location; and a proximal capsule portion configured to maintain a proximal portion of the medical device in a radially-constrained configuration during delivery of the medical device to the deployment location, wherein a proximal end of the proximal capsule portion defines a recess, such that the proximal end of the proximal capsule portion is configured to be retracted such as to overlap with a distal end of the delivery catheter.

11. The apparatus according to claim 10, wherein the delivery device further comprises a handle comprising a rotational control component that is configured to transmit rotational motion to the capsule; and a motion-conversion mechanism disposed within the capsule, the motion-conversion mechanism being configured to convert the rotational motion to axial motion of a portion of the capsule, to thereby release at least a portion of the medical device.

12. The apparatus according to claim 11, wherein the motion-conversion mechanism comprises a screw-and-nut mechanism.

13. An apparatus for use with a medical device comprising:

a delivery device configured to deliver the medical device to a deployment location within a body of a subject, the delivery device comprising:

a capsule configured to house the medical device during delivery of the medical device to the deployment location, the capsule comprising:

a distal capsule portion configured to maintain a distal portion of the medical device in a radially-constrained configuration during delivery of the medical device to the deployment location, the distal capsule portion being coupled to a first shaft; and a proximal capsule portion configured to maintain a proximal portion of the medical device in a radially-constrained configuration during delivery of the medical device to the deployment location, a handle comprising a rotational control component that is configured to transmit rotational motion to the capsule;

a distal device interface configured to secure a distal portion of the medical device, the distal device interface being coupled to a second shaft;

a motion-conversion mechanism disposed within the capsule and configured to cause rotational motion of the first shaft relative to the second shaft to result in axial motion of the first shaft relative to the second shaft, to thereby cause the distal capsule portion to move axially relative to the distal portion of the medical device to thereby release at least a portion of the medical device; and a bearing mechanism that is configured to separate rotational motion of the distal capsule portion from rotational motion of the first shaft.

14. The apparatus according to claim 13, wherein the motion-conversion mechanism comprises a screw-and-nut mechanism.

15. The apparatus according to claim 14, wherein a surface of the first shaft is threaded and a surface of the second shaft is threaded, such that rotational motion of the first shaft relative to the second shaft to result in axial motion of the first shaft relative to the second shaft.

16. The apparatus according to claim 14, wherein a surface of the first shaft is threaded and a surface of the distal device interface is threaded, such that rotational motion of the first shaft relative to the distal device interface to result in axial motion of the first shaft relative to the distal device interface.

* * * * *